United States Patent [19]

Obata et al.

[11] Patent Number: 5,380,744

[45] Date of Patent: Jan. 10, 1995

[54] PHENOXYALKYLAMINE DERIVATIVE AND AGRICULTURAL AND HORTICULTURAL CHEMICAL FOR CONTROLLING NOXIOUS ORGANISMS CONTAINING THE SAME

[75] Inventors: Tokio Obata; Akira Ooka; Katsutoshi Fujii; Shin Suizu, all of Ube, Japan

[73] Assignee: Ube Industries, Ltd., Yamaguchi, Japan

[21] Appl. No.: 221,496

[22] Filed: Apr. 1, 1994

[30] Foreign Application Priority Data

Apr. 2, 1993 [JP] Japan .................. 5-076931
Jan. 6, 1994 [JP] Japan .................. 6-000322

[51] Int. Cl.$^6$ ............... A01N 43/40; A01N 43/56; C07D 231/14; C07D 401/12
[52] U.S. Cl. .................. 514/403; 514/341; 514/406; 546/211; 548/360.1; 548/365.1; 548/374.1
[58] Field of Search ............ 546/211; 548/360.1, 548/374.1, 365.1; 514/341, 403, 406

[56] References Cited

U.S. PATENT DOCUMENTS

| | | |
|---|---|---|
| 4,213,987 | 7/1980 | Nakagami et al. . |
| 4,304,778 | 12/1981 | Nakagami et al. . |
| 4,435,402 | 3/1984 | Tsuji et al. . |
| 4,562,193 | 12/1985 | Yamamoto et al. . |
| 4,845,097 | 7/1989 | Matsumoto et al. . |
| 5,039,692 | 8/1991 | Obata et al. . |

FOREIGN PATENT DOCUMENTS

| | | |
|---|---|---|
| 0356158 | 2/1990 | European Pat. Off. . |
| 0391685 | 10/1990 | European Pat. Off. . |
| 0521409 | 1/1993 | European Pat. Off. . |

OTHER PUBLICATIONS

Chemical Abstracts, vol. 115, No. 23, Dec. 9, 1993, abstract No. 256159f.

Chemical Abstracts, vol. 119, No. 13, Sep. 27, 1993, abstract No. 133483g.

*Primary Examiner*—Robert W. Ramsuer
*Attorney, Agent, or Firm*—Finnegan, Henderson, Farabow, Garrett & Dunner

[57] ABSTRACT

Disclosed are a phenoxyalkylamine compound represented by the formula (I):

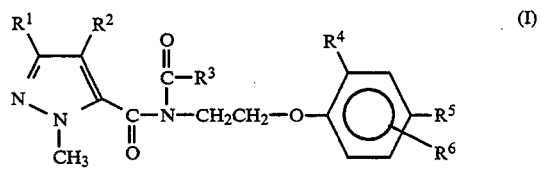

wherein $R^1$ is $C_{1-8}$ alkyl group, $C_{3-8}$ cycloalkyl group, a hydrogen atom, a phenyl group, or $C_{1-4}$ haloalkyl group; $R^2$ is a halogen atom, a hydrogen atom, $C_{1-4}$ alkyl group, $C_{1-4}$ alkoxy group or a nitro group; $R^1$ and $R^2$ may be linked with each other and condensed to a pyrazole ring to form a saturated 4- to 8-membered ring; $R^3$ is $C_{1-15}$ alkyl group, $C_{3-8}$ cycloalkyl group, a phenyl group, $C_{1-4}$ haloalkyl group, $C_{2-8}$ alkoxyalkyl group, $C_{3-6}$ alkenyl group, a pyridyl group, a benzyl group, $C_{3-8}$ alkoxycarbonylalkyl group, a pyrazole group, or $C_{1-4}$ alkoxy group; $R^4$ is $C_{1-4}$ alkyl group, a hydrogen atom or a halogen atom; $R^5$ is $C_{1-20}$ alkyl group, a hydrogen atom, $C_{3-6}$ alkenyl group, a benzyl group, a phenoxy group, a halogen atom, a cyanomethyl group or —A—O—$R^7$ where A is $C_{1-4}$ alkylene group and $R^7$ is $C_{1-6}$ alkyl group, $C_{3-6}$ alkenyl group, $C_{3-6}$ alkynyl group or $C_{2-5}$ acyl group; and $R^6$ is a hydrogen atom, $C_{1-4}$ alkyl group or a halogen atom, a process for preparing the same and a chemical for controlling noxious organisms containing the same as an effective ingredient.

12 Claims, No Drawings

PHENOXYALKYLAMINE DERIVATIVE AND AGRICULTURAL AND HORTICULTURAL CHEMICAL FOR CONTROLLING NOXIOUS ORGANISMS CONTAINING THE SAME

BACKGROUND OF THE INVENTION

This invention relates to a novel N-phenoxyalkyl-substituted pyrazolecarboxamide derivative (hereinafter abbreviated to as "phenoxyalkylamine derivative") which is a chemical for controlling noxious organisms useful as an insecticide, an acaricide and a fungicide.

As phenoxyalkylamine derivatives, there have been disclosed, for example, quinazoline derivatives in Japanese Provisional Patent Publications No. 17123/1979 (which corresponds to U.S. Pat. No. 4,213,987, hereinafter the same), No. 76803/1980 and No. 76804/1980 (both of which correspond to U.S. Pat. No. 4,304,778), a thienopyrimidine derivative in Japanese Provisional Patent Publication No. 42387/1984 (U.S. Pat. No. 4,562,193), pyrimidine derivatives in Japanese Provisional Patent Publications No. 36666/1984, No. 36667/1984 (both of which correspond to U.S. Pat. No. 4,435,402), No. 286373/1986 and No. 67/1987 (both of which correspond to U.S. Pat. No. 4,845,097), and a pyrazole derivative in Japanese Provisional Patent Publication No. 27360/1991 (U.S. Pat. No. 5,039,692).

However, a novel phenoxyalkylamine derivative and a novel phenoxyalkylamide derivative as in the present invention have not been reported.

Thus, a method for synthesizing a phenoxyalkylamine derivative from a phenoxyalkylamide derivative of the present invention has not been known, and it has not been known that the resulting phenoxyalkylamine derivative has an activity of controlling noxious organisms such as an insecticidal, acaricidal or fungicidal activity.

SUMMARY OF THE INVENTION

An object of the present invention is to provide a novel phenoxyalkylamine derivative, a process for preparing the same and an agricultural and horticultural chemical for controlling noxious organisms containing said derivative as an active ingredient, which is useful as an insecticide, an acaricide and a fungicide.

The present inventors have found that a novel phenoxyalkylamine derivative obtained by synthesizing from a novel phenoxyalkylamide derivative has remarkable controlling activities such as insecticidal, acaricidal and fungicidal activities useful as an agricultural and horticultural chemical for controlling noxious organisms, to accomplish the present invention.

That is a first invention is concerned with a phenoxyalkylamine derivative represented by the formula (I):

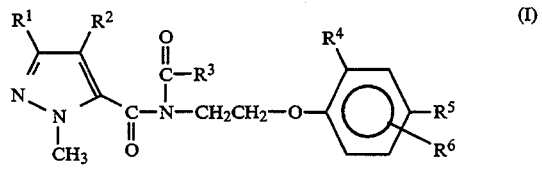

wherein $R^1$ represents an alkyl group having 1 to 8 carbon atoms; a cycloalkyl group having 3 to 8 carbon atoms; a hydrogen atom; a phenyl group which is unsubstituted or substituted by an alkyl group having 1 to 4 carbon atoms or a halogen atom; or a haloalkyl group having 1 to 4 carbon atoms; $R^2$ represents a halogen atom; a hydrogen atom; an alkyl group having 1 to 4 carbon atoms; an alkoxy group having 1 to 4 carbon atoms or a nitro group; $R^1$ and $R^2$ may be linked with each other and fused with carbon atoms of a pyrazole ring to which they are bonded to form a saturated 4- to 8-membered ring which is unsubstituted or substituted by an alkyl group having 1 to 4 carbon atoms; $R^3$ represents an alkyl group having 1 to 15 carbon atoms; a cycloalkyl group having 3 to 8 carbon atoms; a phenyl group which is unsubstituted or substituted by a halogen atom, an alkyl group having 1 to 8 carbon atoms or an alkoxy group having 1 to 4 carbon atoms; a haloalkyl group having 1 to 4 carbon atoms; an alkoxyalkyl group with 2 to 8 carbon atoms in total having an alkoxy group with 1 to 4 carbon atoms; an alkenyl group having 3 to 6 carbon atoms; a pyridyl group which is unsubstituted or substituted by a halogen atom; a benzyl group; an alkoxycarbonylalkyl group with 3 to 8 carbon atoms in total having an alkoxy group with 1 to 4 carbon atoms; a pyrazole group which is unsubstituted or substituted by an alkyl group having 1 to 8 carbon atoms or a halogen atom; or an alkoxy group having 1 to 4 carbon atoms; $R^4$ represents an alkyl group having 1 to 4 carbon atoms; a hydrogen atom or a halogen atom; $R^5$ represents an alkyl group having 1 to 20 carbon atoms; a hydrogen atom; an alkenyl group having 3 to 6 carbon atoms; a benzyl group; a phenoxy group; a halogen atom; a cyanomethyl group or $-A-O-R^7$ where A represents an alkylene group having 1 to 4 carbon atoms and $R^7$ represents an alkyl group having 1 to 6 carbon atoms; an alkenyl group having 3 to 6 carbon atoms, an alkynyl group having 3 to 6 carbon atoms or an acyl group having 2 to 5 carbon atoms; and $R^6$ represents a hydrogen atom; an alkyl group having 1 to 4 carbon atoms or a halogen atom.

A second invention is concerned with a process for preparing the phenoxyalkylamine derivative represented by the above formula (I), which comprises reacting a phenoxyalkylaminepyrazolecarboxylic acid amide derivative represented by the formula (II):

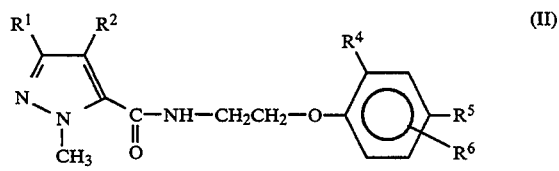

wherein $R^1$, $R^2$ and $R^4$ to $R^6$ have the same meanings as defined above,
with a carboxylic acid halide or an acid anhydride represented by the formula (III):

wherein $R^3$ has the same meaning as defined above; and X represents a halogen atom or a $R^3COO$ group.

A third invention is concerned with a phenoxyalkylamide derivative represented by the formula (IV):

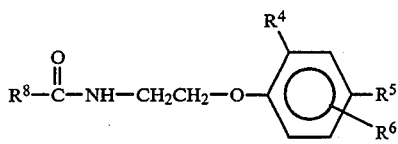

wherein $R^4$ to $R^6$ have the same meanings as defined above; $R^8$ represents an alkyl group having 1 to 15 carbon atoms; a cycloalkyl group having 3 to 8 carbon atoms or a phenyl group which is unsubstituted or substituted by a halogen atom, an alkyl group having 1 to 8 carbon atoms or an alkoxy group having 1 to 4 carbon atoms.

A fourth invention is concerned with a process for preparing the phenoxyalkylamine derivative represented by the above formula (I), which comprises reacting the phenoxyalkylamide derivative represented by the formula (IV') wherein $R^8$ in the above formula (IV) is $R^3$ defined in the formula (I) with a pyrazolecarboxylic acid halide represented by the formula (V):

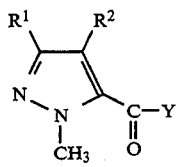

wherein $R^1$ and $R^2$ have the same meanings as defined above; and Y represents a halogen atom.

A fifth invention is concerned with an agricultural and horticultural chemical for controlling noxious organisms comprising the phenoxyalkylamine derivative represented by the above formula (I) as an active ingredient and an insecticidally, acaricidally or fungicidally effective carrier.

DESCRIPTION OF THE PREFERRED EMBODIMENTS

In the following, the present invention is explained in detail.

Desired compound and starting compounds

In the novel phenoxyalkylamine derivative (compound (I)) and starting compounds thereof, $R^1$ to $R^8$, X and Y are as described below.

As $R^1$, there may be mentioned an alkyl group having 1 to 8 carbon atoms, a cycloalkyl group having 3 to 8 carbon atoms, a hydrogen atom, a phenyl group and a haloalkyl group having 1 to 4 carbon atoms.

As the alkyl group, there may be mentioned a straight or branched alkyl group having 1 to 8 carbon atoms, preferably those having 1 to 6 carbon atoms, more preferably those having 1 to 4 carbon atoms.

The cycloalkyl group is preferably a cycloalkyl group having 3 to 6 carbon atoms, more preferably a cyclopropyl group and a cyclobutyl group.

As the phenyl group, there may be mentioned a phenyl group which is unsubstituted or substituted by an alkyl group having 1 to 4 carbon atoms, an alkoxy group having 1 to 4 carbon atoms or a halogen atom, such as o-, m- or p-chlorophenyl group, a p-methylphenyl group, a p-tert-butylphenyl group and a p-methoxyphenyl group.

As the alkyl group to be used as a substituent for the phenyl group, there may be mentioned a straight or branched alkyl group 1 to 4 carbon atoms, preferably a methyl group.

As the alkoxy group to be used as a substituent for the phenyl group, there may be mentioned a straight or branched alkoxy group 1 to 4 carbon atoms, preferably a methoxy group.

As the halogen atom to be used as a substituent, there may be mentioned a chlorine atom, an iodine atom, a bromine atom and a fluorine atom, preferably a chlorine atom.

The position of the above substituent is not particularly limited, but it is preferably 4-position of the phenyl group.

As the haloalkyl group, there may be mentioned a straight or branched haloalkyl group having 1 to 4 carbon atoms, the halogen atom is preferably a fluorine atom, and the alkyl group is preferably a methyl group. The most preferred haloalkyl group is a trifluoromethyl group.

Particularly preferred $R^1$ is an alkyl group having 1 to 4 carbon atoms such as a methyl group, an ethyl group, a propyl group, an isopropyl group, a n-butyl group and a tert-butyl group.

As $R^2$, there may be mentioned a halogen atom, a hydrogen atom, an alkyl group having 1 to 4 carbon atoms, an alkoxy group having 1 to 4 carbon atoms and a nitro group.

As the halogen atom, there may be mentioned a chlorine atom, an iodine atom, a bromine atom and a fluorine atom, preferably a chlorine atom and a bromine atom.

As the alkyl group, there may be mentioned a straight or branched alkyl group having 1 to 4 carbon atoms, preferably a methyl group and an ethyl group.

As the alkoxy group, there may be mentioned a straight or branched alkoxy group having 1 to 4 carbon atoms, preferably a methoxy group.

Particularly preferred $R^2$ is a hydrogen atom or a chlorine atom.

$R^1$ and $R^2$ may be linked with each other and condensed to a pyrazole ring to form a saturated 4- to 8-membered, preferably 4- to 6-membered, more preferably 5-membered ring which is unsubstituted or substituted by an alkyl group having 1 to 4 carbon atoms, with carbon atoms to which they are bonded.

As the alkyl group to be used as a substituent, there may be mentioned a straight or branched alkyl group having 1 to 4 carbon atoms, preferably a methyl group.

As $R^3$, there may be mentioned an alkyl group having 1 to 15 carbon atoms, a cycloalkyl group having 3 to 8 carbon atoms, a phenyl group, a haloalkyl group having 1 to 4 carbon atoms, an alkoxyalkyl group having 2 to 8 carbon atoms, an alkenyl group having 3 to 6 carbon atoms, a pyridyl group, a benzyl group, an alkoxycarbonylalkyl group having 3 to 8 carbon atoms, a pyrazole group and an alkoxy group having 1 to 4 carbon atoms.

As the alkyl group, there may be mentioned a straight or branched alkyl group having 1 to 15 carbon atoms, preferably those having 1 to 10 carbon atoms, more preferably those having 1 to 8 carbon atoms.

The cycloalkyl group is preferably a cycloalkyl group having 3 to 6 carbon atoms such as a cyclopropyl group, a cyclobutyl group, a cyclopentyl group and a cyclohexyl group.

As the phenyl group, there may be mentioned a phenyl group which is unsubstituted or substituted by a halogen atom, an alkyl group having 1 to 6 carbon atoms or an alkoxy group having 1 to 4 carbon atoms.

As the halogen atom to be used as a substituent for the phenyl group, there may be mentioned a chlorine atom, an iodine atom, a bromine atom and a fluorine atom, preferably a chlorine atom.

As the alkyl group to be used as a substituent for the phenyl group, there may be a straight or branched alkyl group having 1 to 8 carbon atoms, preferably those having 1 to 6 carbon atoms, more preferably those having 1 to 4 carbon atoms such as a methyl group, an ethyl group and an isopropyl group.

As the alkoxy group to be used as a substituent for the phenyl group, there may be a straight or branched alkoxy group having 1 to 4 carbon atoms, preferably a methoxy group.

The position of the above substituent is not particularly limited, but it may be 2-position, 3-position or 4-position. When the substituent is an alkyl group or an alkoxy group, the position is preferably 4-position.

Among the phenyl groups which are unsubstituted or substituted represented by $R^3$, there may be most preferred for example, a phenyl group, a 2-chlorophenyl group, a 3-chlorophenyl group, a 4-chlorophenyl group, a 4-methylphenyl group, a 4-tert-butylphenyl group and a 4-methoxyphenyl group.

As the haloalkyl group, there may be mentioned a straight or branched haloalkyl group having 1 to 4 carbon atoms, the halogen atom is preferably a chlorine atom, and the alkyl group is preferably a methyl group. The most preferred haloalkyl group is a chloromethyl group.

As the alkoxyalkyl group, there may be mentioned a straight or branched alkoxyalkyl group having 2 to 8 carbon atoms, the alkoxy group is preferably an alkoxy group having 1 to 4 carbon atoms, more preferably a methoxy group, and the alkyl group is preferably an alkyl group having 1 to 4 carbon atoms, more preferably a methyl group. The most preferred alkoxyalkyl group is a methoxymethyl group.

As the alkenyl group, there may be mentioned a straight or branched alkenyl group having 3 to 6 carbon atoms, preferably those having 3 or 4 carbon atoms (e.g. an allyl group, a 1-propenyl group and a methallyl group), more preferably a 1-propenyl group.

As the pyridyl group, there may be mentioned a pyridyl group which is unsubstituted or substituted by a halogen atom, preferably a 3-pyridyl group.

As the halogen atom to be used as a substituent for the pyridyl group, there may be mentioned a chlorine atom, an iodine atom, a bromine atom and a fluorine atom, preferably a chlorine atom. The substitution position is not particularly limited, but it is preferably 6-position.

As the alkoxycarbonylalkyl group, there may be mentioned a straight or branched alkoxycarbonylalkyl group having 3 to 8 carbon atoms, the alkoxy group is preferably an alkoxy group having 1 to 4 carbon atoms, more preferably an ethoxy group, and the alkyl group is preferably an alkyl group having 1 to 4 carbon atoms, more preferably a methylene group. The most preferred alkoxycarbonylalkyl group is an ethoxycarbonylmethyl group.

As the pyrazole group, there may be mentioned a pyrazole group which is unsubstituted or substituted by an alkyl group having 1 to 8 carbon atoms or a halogen atom, preferably a 5-pyrazole group.

As the alkyl group to be used as a substituent for the pyrazole group, there may be mentioned a straight or branched alkyl group having 1 to 8 carbon atoms, preferably those having 1 to 6 carbon atoms, more preferably those having 1 to 4 carbon atoms. The position of the substituent is not particularly limited, but it is preferably 1-position or 3-position.

As the halogen atom to be used as a substituent for the pyrazole group, there may be mentioned a chlorine atom, an iodine atom, a bromine atom and a fluorine atom, preferably a chlorine atom. The substitution position is not particularly limited, but it is preferably 4-position.

As the alkoxy group, there may be mentioned a straight or branched alkoxy group having 1 to 4 carbon atoms, preferably a methoxy group.

Among these, particularly preferred $R^3$ is an alkyl group having 1 to 3 carbon atoms such as a methyl group, an ethyl group and an isopropyl group or a cycloalkyl group having 3 or 4 carbon atoms such as a cyclopropyl group and a cyclobutyl group.

As $R^4$, there may be mentioned an alkyl group having 1 to 4 carbon atoms, a hydrogen atom and a halogen atom.

As the alkyl group, there may be mentioned a straight or branched alkyl group having 1 to 4 carbon atoms, preferably a methyl group.

As the halogen atom, there may be mentioned a chlorine atom, an iodine atom, a bromine atom and a fluorine atom, preferably a chlorine atom.

Particularly preferred $R^4$ is a methyl group.

As $R^5$ there may be mentioned an alkyl group having 1 to 20 carbon atoms, a hydrogen atom, an alkenyl group having 3 to 6 carbon atoms, a benzyl group, a phenoxy group, a halogen atom, a cyanomethyl group and —A—O—$R^7$.

As the alkyl group, there may be mentioned a straight or branched alkyl group having 1 to 20 carbon atoms, preferably those having 1 to 15 carbon atoms, more preferably those having 1 to 10 carbon atoms.

As the alkenyl group, there may be mentioned a straight or branched alkenyl group having 3 to 6 carbon atoms, preferably those having 3 or 4 carbon atoms, more preferably an allyl group.

As the halogen atom, there may be mentioned a chlorine atom, an iodine atom, a bromine atom and a fluorine atom, preferably a chlorine atom.

As the substituent A in —A—O—$R^7$, there may be mentioned an alkylene group having 1 to 4 carbon atoms, and as $R^7$, there may be mentioned an alkyl group having 1 to 6 carbon atoms, an alkenyl group having 3 to 6 carbon atoms, an alkynyl group having 3 to 6 carbon atoms and an acyl group having 2 to 5 carbon atoms.

As the substituent A, there may be mentioned a straight or branched alkylene group having 1 to 4 carbon atoms, preferably an ethylene group.

As the alkyl group represented by $R^7$, there may be mentioned a straight or branched alkyl group having 1 to 6 carbon atoms, preferably those having 1 to 4 carbon atoms, more preferably those having 1 to 3 carbon atoms.

As the alkenyl group represented by $R^7$, there may be mentioned a straight or branched alkenyl group having 3 to 6 carbon atoms, preferably those having 3 or 4 carbon atoms, more preferably an allyl group.

As the alkynyl group represented by $R^7$, there may be mentioned a straight or branched alkynyl group having 3 to 6 carbon atoms, those having 3 or 4 carbon atoms (e.g. a 1-propynyl group, a 2-propynyl group and a 2-butynyl group), more preferably a 2-propynyl group.

As the acyl group represented by $R^7$, there may be mentioned an acetyl group having 2 to 5 carbon atoms such as an acetyl group, a-n-propionyl group, an isopropionyl group, a n-butyryl group, an isobutyryl group, a sec-butyryl group and a tert-butyryl group, preferably those having 2 to 4 carbon atoms, most preferably an acetyl group.

Particularly preferred $R^7$ is a methyl group, an ethyl group, a n-propyl group, an allyl group and a 2-propynyl group.

As —A—O—$R^7$, there may be most preferred, for example, a 2-methoxyethyl group, a 2-ethoxyethyl group, a 2-propoxyethyl group, a 2-allyloxy group and a 2-propargyloxyethyl group.

As $R^6$, there may be mentioned a hydrogen atom, an alkyl group having 1 to 4 carbon atoms and a halogen atom.

As the alkyl group, there may be mentioned a straight or branched alkyl group having 1 to 4 carbon atoms, preferably a methyl group. The position of the substituent is not particularly limited, but it is preferably 3-position or 6-position.

As the halogen atom, there may be mentioned a chlorine atom, an iodine atom, a bromine atom and a fluorine atom, preferably a chlorine atom. The position of the substituent is not particularly limited, but it is preferably 6-position.

Particularly preferred $R^6$ is a hydrogen atom.

As $R^8$, there may be mentioned an alkyl group having 1 to 15 carbon atoms, a cycloalkyl group having 3 to 8 carbon atoms and a phenyl group.

As the alkyl group, there may be mentioned a straight or branched alkyl group having 1 to 15 carbon atoms, preferably those having 1 to 10 carbon atoms, mope preferably those having 1 to 8 carbon atoms.

The cycloalkyl group is preferably a cycloalkyl group having 3 to 6 carbon atoms, more preferably 3 or 4 carbon atoms.

As the phenyl group, there may be mentioned a phenyl group which is unsubstituted or substituted by a halogen atom, an alkyl group having 1 to 8 carbon atoms or an alkoxy group having 1 to 4 carbon atoms.

As the halogen atom to be used as a substituent, there may be mentioned a chlorine atom, an iodine atom, a bromine atom and a fluorine atom, preferably a chlorine atom, a bromine atom and a fluorine atom. The position of the substituent is not particularly limited, but it is preferably 2-position, 3-position or 4-position when the substituent is a chlorine atom; it is preferably 4-position when the substituent is a bromine atom; and it is preferably 2-position or 6-position when the substituent is a fluorine atom.

As the alkyl group to be used as a substituent, there may be mentioned a straight or branched alkyl group having 1 to 8 carbon atoms, preferably those having 1 to 6 carbon atoms, more preferably those having 1 to 4 carbon atoms. The position of the substituent is not particularly limited, but it is preferably 3-position or 4-position.

X represents a halogen atom such as a chlorine atom, an iodine atom, a bromine atom and a fluorine atom or a $R^3COO$ group where $R^3$ has the same meaning as defined above, and preferably a chlorine atom.

Y represents a halogen atom such as a chlorine atom, an iodine atom, a bromine atom and a fluorine atom, and preferably a chlorine atom.

Synthesis of compound (I)

The compound (I) can be synthesized according to Synthetic method 1 or 2 shown below.

(Synthetic method 1)

The compound (I) can be synthesized as shown below by reacting the compound (II) with the compound (III) in the presence or absence of a solvent. For the purpose of accelerating the reaction, it is preferred to carry out the reaction in the presence of a base when X of the compound (III) is a halogen atom, and it is preferred to carry out the reaction in the presence of an acid catalyst when X is a $R^3COO$ group.

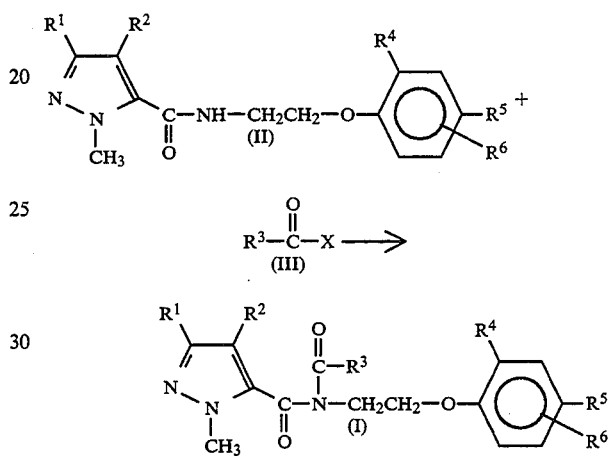

wherein $R^1$ to $R^6$ and X have the same meanings as defined above.

The solvent is not particularly limited so long as it does not participate in the present reaction directly, and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as diethyl ether, tetrahydrofuran and dioxane; ketones such as acetone and methyl ethyl ketone; amides such as N,N-dimethylformamide and N,N-dimethylacetamide; nitriles such as acetonitrile and propionitrile; organic bases such as triethylamine, pyridine and N,N-dimethylaniline; 1,3-dimethyl-2-imidazolidinone; dimethyl sulfoxide; and a mixture of the above solvents.

The solvent may be used in such an amount that the concentration of the compound (II) becomes 5 to 80% by weight, preferably 10 to 70% by weight.

The base is not particularly limited, and may include, for example, organic bases such as triethylamine, pyridine, N,N-dimethylaniline and 1,8-diazabicyclo[5.4.0]-7-undecene (DBU); alkali metal alkoxides such as sodium methoxide and sodium ethoxide; and inorganic bases such as sodium hydride, sodium amide, sodium hydroxide, potassium hydroxide, sodium carbonate, sodium hydrogen carbonate and potassium carbonate. Preferred are organic bases.

The amount of the base to be used may be 0.001 to 5 mole, preferably 0.8 to 5 mole per mole of the compound (II).

As the acid catalyst, there may be mentioned sulfuric acid, benzenesulfonic acid and p-toluenesulfonic acid.

The amount of the acid catalyst to be used may be a catalytic amount.

The reaction temperature is not particularly limited, but it may be in the temperature range of ice cooling temperature to a boiling point or lower of a solvent used, preferably 50° to 100° C.

The reaction time varies depending on the above concentration and temperature, but it is generally 0.5 to 10 hours.

The amount of the compound (III) to be used is 0.5 to 2 mole, preferably 1.0 to 1.5 mole per mole of the compound (II).

The compound (II) can be prepared according to, for example, the method described in Japanese Provisional Patent Publication No. 27360/1991 by using a phenoxyalkylamine and a pyrazolecarboxylic acid halide as shown below.

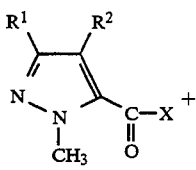

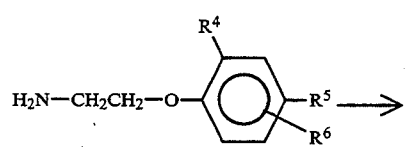

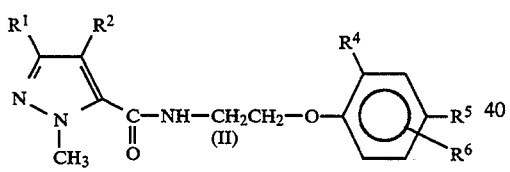

wherein $R^1$, $R^2$, $R^4$ to $R^6$ and X have the same meanings as defined above.

The phenoxyalkylamine can be synthesized by using a phenoxyalkyl halide as in the synthesis of the compound (VI) shown below.

The pyrazolecarboxylic acid halide can be obtained by reacting a pyrazolecarboxylic acid and a thionyl halide ($SOX_2$ where X has the same meaning as defined above).

As the compound (II), there may be mentioned, for example, the respective compounds having $R^1$, $R^2$, $R^4$, $R^5$ and $R^6$ shown in Tables 1 and 2, preferably the compounds (II) comprising the respective kinds of substituents corresponding to Compounds 1 to 125 shown in Table 2 (referred to as Compound (II)$_1$ to Compound (II)$_{125}$, and, for example, Compound (II)$_1$ is a compound in which $R^1$ is a methyl group, $R^2$ is a chlorine atom, $R^4$ is a methyl group, $R^5$ is a methyl group and $R^6$ a hydrogen atom).

The compound (III) in which X is a $R^3COO$ group may be obtained from commercially available products.

The compound (III) in which X is a halogen atom can be prepared by a known method shown below.

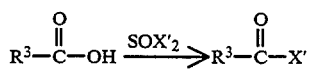

wherein $R^3$ has the same meaning as defined above; and X' represents a halogen atom.

As the compound (III), there may be mentioned, for example, the compounds (III) comprising the respective kinds of substituents corresponding to Compounds 1 to 125 shown in Table 2 (referred to as Compound (III)$_1$ to Compound (III)$_{125}$, and, for example, Compound (III)$_1$ is a compound in which $R^3$ is a methyl group and X is a halogen atom or an acetyloxy group).

(Synthetic method 2)

The compound (I) can be synthesized as shown below by reacting the compound (IV') with the compound (V) in the presence or absence of a solvent. The compound (IV) is preferably used in place of the compound (IV'), i.e., $R^3$ in the formula (IV') is preferably $R^8$, and for the purpose of accelerating the reaction, it is preferred to carry out the reaction in the presence of a base.

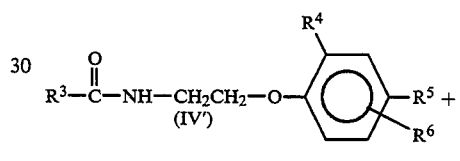

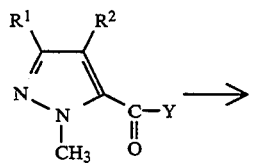

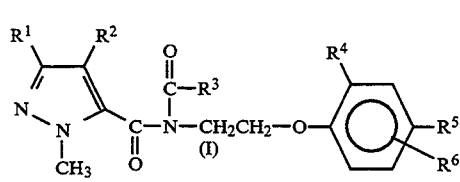

wherein $R^1$ to $R^6$ have the same meanings as defined above; and Y represents a halogen atom.

The kinds and amounts of the solvent and the base, the reaction temperature, the reaction time, the amounts of the starting compounds to be used are the same as in Synthetic method 1.

The compound (IV) can be synthesized as shown below generally by reacting the compound (VI) with the compound (VII) in the presence or absence of a solvent. For the purpose of accelerating the reaction, it is preferred to carry out the reaction in the presence of a base when X is a halogen atom, and it is preferred to carry out the reaction in the presence of an acid catalyst when X is a $R^8COO$ group. The compound (IV') can be prepared in the same manner as mentioned below by using the compound (III) in place of the compound (VII).

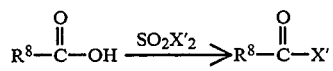

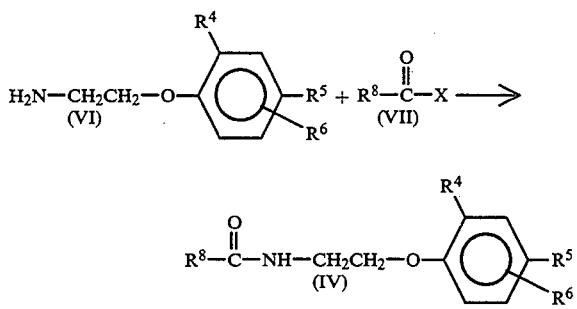

wherein $R^4$ to $R^6$, $R^8$ and X have the same meanings as defined above.

The kinds and amounts of the solvent and the acid catalyst are the same as in Synthetic method 1.

The same base as in Synthetic method 1 can be used. The amount of the base to be used is 0.001 to 5 mole, preferably 0.8 to 1.5 mole per mole of the compound (VI).

The reaction temperature is not particularly limited, but it may be in the temperature range of ice cooling temperature to a boiling point or lower of a solvent used, preferably ice cooling temperature to room temperature.

The reaction time varies depending on the above concentration of the reactants and temperature, but it is generally 0.3 to 2 hours.

The amount of the compound (VII) to be used is 0.5 to 2 mole, preferably 1.0 to 1.2 mole per mole of the compound (VI).

The compound (VI) can be prepared by, for example, using a phenoxyalkyl halide as shown below.

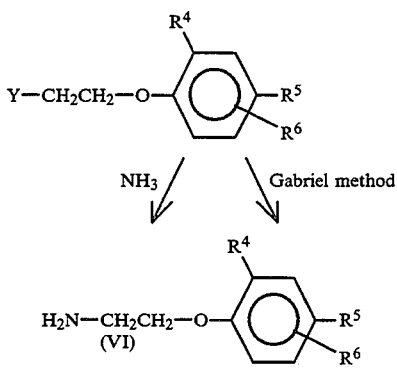

wherein $R^4$ to $R^6$ and Y have the same meanings as defined above.

As the compound (VI), there may be mentioned, for example, the compounds having $R^4$ to $R^6$ shown in Tables 1 and 2, preferably the compounds (VI) comprising the respective kinds of substituents shown in Table 1 (referred to as Compound (VI)$_1$ to Compound (VI)$_{37}$, and, for example, Compound (VI)$_1$ is a compound in which $R^4$ is a methyl group, $R^5$ is —CH$_2$CH$_2$OC$_2$H$_5$ and $R^6$ a hydrogen atom).

The compound (VII) in which X is a $R^3$COO group may be obtained from commercially available products.

The compound (VII) in which X is a halogen atom can be prepared by a known method shown below.

$$R^8-\overset{O}{\underset{\|}{C}}-OH \xrightarrow{SO_2X'_2} R^8-\overset{O}{\underset{\|}{C}}-X'$$

wherein $R^8$ and X' have the same meanings as defined above.

As the compound (VII), there may be mentioned, for example, the compounds (VII) having $R^8$ shown in Table 1 (referred to as Compound (VII)$_1$ to Compound (VII)$_{37}$, and, for example, Compound (VII)$_1$ is a compound in which $R^8$ is a methyl group and X is a halogen atom).

As the compound (IV) thus obtained, there may be mentioned, for example, the compounds having $R^4$ to $R^6$ and $R^8$ shown in Tables 1 and 2, preferably the compounds (IV) comprising the respective kinds of substituents shown in Table 1 (referred to as Compound (IV-1) to Compound (IV-37), and, for example, Compound (IV-1) is a compound in which $R^4$ and $R^8$ are methyl groups, $R^5$ is —CH$_2$CH$_2$OC$_2$H$_5$ and $R^6$ is a hydrogen atom).

The compound (V) can be obtained by reacting a pyrazolecarboxylic acid and a thionyl halide (SOY$_2$ where Y has the same meaning as defined above).

As the compound (V), there may be mentioned, for example, the compounds (V) comprising the respective kinds of substituents corresponding to Compounds 1 to 125 shown in Table 2 (referred to as Compound (V)$_1$ to Compound (V)$_{125}$, and, for example, Compound (V)$_1$ is a compound in which $R^1$ is a methyl group, $R^2$ is a chlorine atom and Y is a halogen atom).

After completion of the reaction, the desired compound (I) prepared as described above is subjected to common post-treatments such as extraction, condensation and filtration, and if necessary, it may be purified suitably by a known means such as recrystallization and various chromatographic means.

As the compound (I), there may be mentioned, for example, the compounds (I) having $R^1$ to $R^6$ shown in Tables 1 and 2, preferably the compounds (I) comprising the respective kinds of substituents shown in Table 2 (for example, Compound 1 is a compound in which $R^1$, $R^3$, $R^4$ and $R^5$ are methyl groups, $R^2$ is a chlorine atom and $R^6$ is a hydrogen atom).

Agricultural and horticultural chemical for controlling noxious organisms

As the noxious organisms on which a controlling effect by the compound (I) of the present invention can be observed, there may be mentioned agricultural and horticultural noxious insects (e.g. Hemiptera (planthoppers, leafhoppers, aphids and whiteflies), Lepidoptera (cabbage armyworms, diamond-back moth, leafroller moths, pyralid moths and common cabbage worm), Coleoptera (Tenebrionid beetles, leafbeetles, weevils and scarabs) and Acarina (citrus red mite and two-spotted spider mite of Tetranychidae family and pink citrus rust mite of Eriophyidae family)), hygienically noxious insects (e.g. flies, mosquitoes and cockroaches), noxious insects of stored grains (rust-red flour beetles and bean weevils), and root knot nematode, pine wood nematode and bulb mite in soil, and also agricultural and horticultural diseases (e.g. brown rust (wheat), powdery mildew (barley), downy mildew (cucumber), blast (rice) and late blight (tomato)).

Chemical for controlling noxious organisms

The chemical for controlling noxious organisms of the present invention has remarkable insecticidal, acaricidal and fungicidal effects, and contains at least one compound (I) as an active ingredient.

The compound (I) can be used singly, but may be preferably used by mixing with a carrier, a surfactant, a dispersant and an auxiliary (for example, prepared as a composition such as a dustable powder, an emulsifiable concentrate, a fine granule, a granule, a wettable powder, an oily suspension and an aerosol) according to a conventional method.

As the carrier, any insecticidally, acaricidally or fungicidally effective carrier may be used, and there may be mentioned, for example, a solid carrier such as talc, bentonite, clay, kaolin, diatomaceous earth, white carbon, vermiculite, calcium hydroxide, siliceous sand, ammonium sulfate and urea; a liquid carrier such as hydrocarbons (e.g. kerosine and mineral oil) aromatic hydrocarbons (e.g. benzene, toluene and xylene), chlorinated hydrocarbons (e.g. chloroform and carbon tetrachloride), ethers (e.g. dioxane and tetrahydrofuran), ketones (e.g. acetone, cyclohexanone and isophorone), esters (e.g. ethyl acetate, ethylene glycol acetate and dibutyl maleate), alcohols (e.g. methanol, n-hexanol and ethylene glycol), polar solvents (e.g. dimethylformamide and dimethyl sulfoxide) and water; and a gas carrier such as air, nitrogen, carbon dioxide and freon (trade name, produced by Du Pont de Nemours & Co. Inc.) (in the case of a gas carrier, mixed spray can be carried out).

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignosulfonate and polyoxyethylene glycol ether. Further, for improving properties of its formulation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into formulations, the concentration of the active ingredient is generally 1 to 50% by weight in an emulsifiable concentrate, generally 0.3 to 25% by weight in a dustable powder, generally 1 to 90% by weight in a wettable powder, generally 0.5 to 5% by weight in a granule, generally 0.5 to 5% by weight in an oily suspension, and generally 0.1 to 5% by weight in an aerosol.

These formulations can be provided for various uses by diluting them to have a suitable concentration and spraying them to stems and leaves of plants, soil and paddy field surface, or by applying them directly thereto, depending on the purposes.

EXAMPLES

The present invention is described in detail by referring to Examples, but the scope of the present invention is not limited by these Examples.

Example 1 (Syntheses of compounds (IV))

(1) Synthesis of N-{2-[4-(2-ethoxyethyl)-2-methylphenoxy]ethyl}acetamide (Compound (IV-1))

In 50 ml of toluene were dissolved 10.0 g of 2-[4-(2-ethoxyethyl)-2-methylphenoxy]ethylamine and 5.0 g of triethylamine, and 20 ml of a toluene solution containing 3.6 g of acetyl chloride was added dropwise to the solution under ice cooling and stirring. The mixture was stirred at room temperature for 1 hour.

After completion of the reaction, 50 ml of water was added to the reaction mixture. The toluene layer was collected by separation, washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene: ethyl acetate=4:1) to obtain 10.3 g of the title compound as colorless powdery crystals.

$^1$H-NMR (CDCl$_3$, δppm) 1.20 (t, 3H), 2.00 (s, 3H), 2.20 (s, 3H), 2.80 (t, 2H), 3.50 (t-d, 2H), 3.57 (t, 2H), 3.65 (q, 2H), 4.00 (t, 2H), 6.08 (s, 1H), 6.72 (d, 1H), 6.98 (d, 1H), 7.00 (s, 1H)

(2) Synthesis of N-{2- [4-(2-ethoxyethyl)-2,3-dimethylphenoxy]ethyl}acetamide (Compound (IV-4))

In 30 ml of toluene were dissolved 4.7 g of 2-[4-(2-ethoxyethyl)-2,3-dimethylphenoxy]ethylamine and 2.2 g of triethylamine, and 10 ml of a toluene solution containing 1.3 g of acetyl chloride was added dropwise to the solution under ice cooling and stirring. The mixture was stirred at room temperature for 1 hour.

After completion of the reaction, 40 ml of water was added to the reaction mixture. The toluene layer was collected by separation, washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene: ethyl acetate=4:1) to obtain 5.1 g of the title compound as colorless powdery crystals.

$^1$H-NMR (CDCl$_3$, δppm) 1.20 (t, 3H), 2.00 (s, 3H), 2.18 (s, 3H), 2.23 (s, 3H), 2.88 (t, 2H), 3.47 to 3.67 (m, 4H), 4.01 (t, 2H), 5.97 (s, 1H), 6.63 (d, 1H), 6.98 (d, 1H)

(3) Synthesis of N-{2- [4-(2-ethoxyethyl)-2,3-dimethylphenoxy]ethyl}isobutylamide (Compound (IV-7))

In 30 ml of toluene was dissolved 2.37 g of 2-[4-(2-ethoxyethyl)-2,3-dimethylphenoxy]ethylamine, and 1.6 g of isobutyric anhydride was added dropwise to the solution at room temperature under stirring. The mixture was stirred at room temperature for 1 hour.

After completion of the reaction, the reaction mixture was washed with water, washed with a saturated sodium hydrogen carbonate aqueous solution and further washed with water, and then dried over anhydrous sodium sulfate. Then, the solvent was removed under reduced pressure.

The resulting crystals were recrystallized from toluene-n-hexane to obtain 2.8 g of the title compound as colorless needle crystals.

(4) Syntheses of other compounds (IV) in Table 1

According to the methods described in the above (1) to (3), the other compounds (IV) in Table 1 shown below were synthesized.

TABLE 1

$$R^8-\underset{\underset{O}{\|}}{C}-NH-CH_2CH_2-O-\underset{\underset{R^6}{}}{\overset{R^4}{\bigcirc}}-R^5 \quad (IV)$$

| Compound | $R^4$ | $R^5$ | $R^6$ | $R^8$ | Physical property |
|---|---|---|---|---|---|
| (IV - 1) | $CH_3$ | $-CH_2CH_2OC_2H_5$ | H | $CH_3$ | m.p. 46 to 48° C. |
| (IV - 2) | $CH_3$ | $-CH_2CH_2OC_2H_5$ | H |  | m.p. 63.0 to 64.5° C. |
| (IV - 3) | $CH_3$ | $-CH_2CH_2OC_2H_5$ | H |  | m.p. 63.5 to 65.0° C. |
| (IV - 4) | $CH_3$ | $-CH_2CH_2OC_2H_5$ | 3-$CH_3$ | $CH_3$ | m.p. 78.5 to 80.5° C. |
| (IV - 5) | $CH_3$ | $-CH_2CH_2OC_2H_5$ | 3-$CH_3$ | $C_2H_5$ | m.p. 71 to 73° C. |
| (IV - 6) | $CH_3$ | $-CH_2CH_2OC_2H_5$ | 3-$CH_3$ | n-$C_3H_7$ | m.p. 47 to 49° C. |
| (IV - 7) | $CH_3$ | $-CH_2CH_2OC_2H_5$ | 3-$CH_3$ | i-$C_3H_7$ | m.p. 91 to 92° C. |
| (IV - 8) | $CH_3$ | $-CH_2CH_2OC_2H_5$ | 3-$CH_3$ | n-$C_4H_9$ | m.p. 55 to 57° C. |
| (IV - 9) | $CH_3$ | $-CH_2CH_2OC_2H_5$ | 3-$CH_3$ | t-$C_4H_9$ | m.p. 53 to 55° C. |
| (IV - 10) | $CH_3$ | $-CH_2CH_2OC_2H_5$ | 3-$CH_3$ | n-$C_5H_{11}$ | m.p. 50 to 51° C. |
| (IV - 11) | $CH_3$ | $-CH_2CH_2OC_2H_5$ | 3-$CH_3$ | n-$C_8H_{17}$ | m.p. 61 to 62° C. |
| (IV - 12) | $CH_3$ | $-CH_2CH_2OCH_3$ | H | $CH_3$ | $n_D^{16.0}$ 1.5317 |
| (IV - 13) | $CH_3$ | $-CH_2CH_2OC_3H_7$-n | H | $CH_3$ | m.p. 53 to 54° C. |
| (IV - 14) | $CH_3$ | $-CH_2CH_2OCH_2CH=CH_2$ | H | $CH_3$ | $n_D^{16.1}$ 1.5229 |
| (IV - 15) | $CH_3$ | $-CH_2CH_2OCH_2C\equiv CH$ | H | $CH_3$ | m.p. 70 to 72° C. |
| (IV - 16) | $CH_3$ | $-CH_2CH_2OC_2H_5$ | 6-$CH_3$ | $CH_3$ | $n_D^{16.1}$ 1.5149 |
| (IV - 17) | $CH_3$ | $-CH_2CH_2OC_2H_5$ | H | $C_2H_5$ | $n_D^{22.1}$ 1.5118 |
| (IV - 18) | $CH_3$ | $-CH_2CH_2OC_2H_5$ | H | n-$C_3H_7$ | $n_D^{22.1}$ 1.5084 |
| (IV - 19) | $CH_3$ | $-CH_2=CHCH_2$ | H | $CH_3$ | $n_D^{16.1}$ 1.5325 |
| (IV - 20) | $CH_3$ | n-$C_3H_7$ | H | $CH_3$ | m.p. 39 to 41° C. |
| (IV - 21) | $CH_3$ | n-$C_4H_9$ | H | $CH_3$ | $n_D^{16.5}$ 1.5179 |
| (IV - 22) | $CH_3$ | n-$C_4H_9$ | 6-Cl | $CH_3$ | $n_D^{17.0}$ 1.5225 |
| (IV - 23) | $CH_3$ | i-$C_4H_9$ | H | $CH_3$ | $n_D^{17.0}$ 1.5155 |
| (IV - 24) | $CH_3$ | n-$C_5H_{11}$ | H | $CH_3$ | m.p. 54 to 55° C. |
| (IV - 25) | $CH_3$ | i-$C_5H_{11}$ | H | $CH_3$ | $n_D^{17.3}$ 1.5139 |
| (IV - 26) | $CH_3$ | n-$C_8H_{17}$ | H | $CH_3$ | m.p. 53 to 55° C. |
| (IV - 27) | $CH_3$ | n-$C_{10}H_{21}$ | H | $CH_3$ | m.p. 61 to 63° C. |
| (IV - 28) | $CH_3$ | $-CH_2CH_2OC_2H_5$ | 3-$CH_3$ | 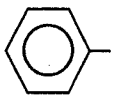 | m.p. 69 to 71° C. |
| (IV - 29) | $CH_3$ | $-CH_2CH_2OC_2H_5$ | 3-$CH_3$ | 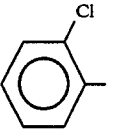 | m.p. 59 to 61° C. |
| (IV - 30) | $CH_3$ | $-CH_2CH_2OC_2H_5$ | 3-$CH_3$ | 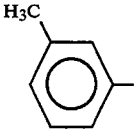 | m.p. 46 to 48° C. |

TABLE 1-continued $$R^8-\overset{O}{\underset{\|}{C}}-NH-CH_2CH_2-O-\underset{R^6}{\overset{R^4}{\underset{}{\bigcirc}}}-R^5 \quad (IV)$$

| Compound | $R^4$ | $R^5$ | $R^6$ | $R^8$ | Physical property |
|---|---|---|---|---|---|
| (IV - 31) | $CH_3$ | $-CH_2CH_2OC_2H_5$ | 3-$CH_3$ | Br-⟨◯⟩- | m.p. 76 to 78° C. |
| (IV - 32) | $CH_3$ | $-CH_2CH_2OC_2H_5$ | 3-$CH_3$ | $H_3C$-⟨◯⟩- | m.p. 67 to 69° C. |
| (IV - 33) | $CH_3$ | $-CH_2CH_2OC_2H_5$ | 3-$CH_3$ | t-$H_9C_4$-⟨◯⟩- | m.p. 95 to 96° C. |
| (IV - 34) | H | $-CH_2CH_2OCH_3$ | H | $CH_3$ | $n_D^{22.2}$ 1.5220 |
| (IV - 35) | H | n-$C_5H_{11}$ | H | $CH_3$ | m.p. 49 to 51° C. |
| (IV - 36) | $CH_3$ | $-CH_2CH_2OC_2H_5$ | 3-$CH_3$ | $H_3CO$-⟨◯⟩- | m.p. 63 to 65° C. |
| (IV - 37) | $CH_3$ | $-CH_2CH_2OC_2H_5$ | H | F-⟨◯⟩-F | m.p. 80 to 82° C. |

Example 2 (Syntheses of compounds (I))

(1) Synthesis of N-acetyl-N-[2-(2,4-dimethylphenoxy)-ethyl]-4-chloro-1,3-dimethyl-5-pyrazolecarboxamide (Compound 1)

In 10 ml of dried N,N-dimethylformamide was dissolved 1.3 g of N-2-(2,4-dimethylphenoxy)-4-chloro-1,3-dimethyl-5-pyrazolecarboxamide. 0.3 g of sodium hydride (60% in oil) was added to the solution, and the mixture was stirred at 100° C. for 1 hour. The mixture was cooled to room temperature and 0.5 g of acetyl chloride was added dropwise to the mixture. Then, the mixture was stirred at 100° C. for 1 hour.

After completion of the reaction, 10 ml of water was slowly added to the reaction mixture, and the mixture was extracted with ethyl acetate. The extract was washed with water and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene: ethyl acetate=9:1) to obtain 0.8 g of the title compound as pale yellow oily liquid.

$^1$H-NMR (CDCl$_3$, δppm) 2.06 (s, 3H), 2.21 (s, 3H), 2.22 (s, 3H), 2.39 (s, 3H), 3.86 (s, 3H), 4.08 to 4.22 (m, 4H), 6.65 (d, 1H), 6.91 (s, 1H), 6.93 (s, 1H)

(2) Synthesis of N-acetyl-N-{2-[4-(2-methoxyethyl)-2-methylphenoxy]ethyl}-4-bromo-1,3-dimethyl-5-pyrazolecarboxamide (Compound 4)

In 8 ml of acetic anhydride was dissolved 1.1 g of N-{2-[4-( 2-methoxyethyl)-2-methylphenoxy]ethyl}-4-bromo-1,3-dimethyl-5-pyrazolecarboxamide. 0.05 ml g of conc. sulfuric acid was added to the solution, and the mixture was stirred at 100° C. for 4 hours.

After completion of the reaction, the reaction mixture was cooled to room temperature and made weakly acidic by adding a saturated sodium carbonate aqueous solution. The mixture was extracted with ethyl acetate, and the extract was washed with water and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene: ethyl acetate=9:1) to obtain 0.8 g of the title compound as pale yellow oily liquid.

$^1$H-NMR (CDCl$_3$, δppm) 2.09 (s, 3H), 2.23 (s, 3H), 2.39 (s, 3H), 2.78 (t, 3H), 3.33 (s, 3H), 3.55 (t, 2H), 4.10 to 4.25 (m, 4H), 6.70 (d, 1H), 6.96 (d, 1H), 6.97 (s, 1H)

(3) Synthesis of N-propionyl-N-{2-[4-(2-methoxyethyl)-2-methylphenoxy]ethyl}-4-chloro-1,3-dimethyl-5-pyrazolecarboxamide (Compound 5)

In 10 ml of dried N,N-dimethylformamide was dissolved 1.1 g of N-{2-[4-(2-methoxyethyl)-2-methylphenoxy]ethyl}-4-chloro-1,3-dimethyl-5-pyrazolecarboxamide. 0.3 g of sodium hydride (60% in oil) was added to the solution, and the mixture was stirred at 100° C. for 1 hour. The mixture was cooled to room temperature and 0.4 g of propionyl chloride was added dropwise to the mixture. Then, the mixture was stirred at 100° C. for 1 hour.

After completion of the reaction, 10 ml of water was slowly added to the reaction mixture, and the mixture was extracted with ethyl acetate. The extract was washed with water and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene: ethyl acetate=9:1) to obtain 0.7 g of the title compound as pale yellow oily liquid.

$^1$H-NMR (CDCl$_3$, δppm) 1.19 (t, 3H), 2.08 (s, 3H), 2.22 (s, 3H), 2.73 (q, 3H), 2.78 (t, 2H), 3.33 (s, 3H), 3.56 (t, 2H), 3.88 (s, 3H), 4.10 to 4.25 (m, 4H), 6.70 (d, 1H), 6.97 (d, 1H), 6.98 (s, 1H)

(4) Synthesis of N-benzoyl-N-{2-[4-(2-methoxyethyl)-2-methylphenoxy]ethyl}-4-chloro-1,3-dimethyl-5-pyrazolecarboxamide (Compound 6)

In 10 ml of dried toluene was dissolved 1.2 g of N-{2-[4-(2-methoxyethyl)-2-methylphenoxy]ethyl}-4-chloro-1,3-dimethyl-5-pyrazolecarboxamide. 0.25 g of sodium hydride (60% in oil) was added to the solution, and the mixture was refluxed under heating for 2 hours. The mixture was cooled to room temperature and 0.6 g of benzoyl chloride was added dropwise to the mixture. Then, the mixture was refluxed under heating for 1 hour.

After completion of the reaction, 10 ml of water was added slowly to the reaction mixture, and the mixture was extracted with ethyl acetate. The extract was washed with water and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene: ethyl acetate=9:1) to obtain 1.4 g of the title compound as pale yellow oily liquid.

$^1$H-NMR (CDCl$_3$, δppm) 1.19 (s, 3H), 1.92 (s, 3H), 2.78 (t, 3H), 3.35 (s, 3H), 3.56 (t, 2H), 3.75 (s, 3H), 4.30 to 4.60 (m, 4H), 6.76 (d, 1H), 6.91 (d, 1H), 7.00 (d-d, 1H), 7.26 (2H), 7.35 (1H), 7.50 (d, 2H)

(5) Synthesis of N-acetyl-N-{2-[4-(2-ethoxyethyl)-2-methylphenoxy]ethyl}-4-chloro-1,3-dimethyl-5-pyrazolecarboxamide (Compound 7)

In 10 ml of dried N,N-dimethylformamide was dissolved 1.2 g of N-{2-[4-(2-ethoxyethyl)-2-methylphenoxy]ethyl}-4-chloro-1,3-dimethyl-5-pyrazolecarboxamide. 0.3 g of sodium hydride (60% in oil) was added to the solution, and the mixture was stirred at 50° C. for 1 hour. The mixture was cooled to room temperature and 0.4 g of acetyl chloride was added dropwise to the mixture. Then, the mixture was stirred at 50° C. for 2 hours.

After completion of the reaction, 10 ml of water was added slowly to the reaction mixture, and the mixture was extracted with ethyl acetate. The extract was washed with water and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene: ethyl acetate=9:1) to obtain 0.6 g of the title compound as pale yellow oily liquid.

$^1$H-NMR (CDCl$_3$, δppm) 1.20 (t, 3H), 2.08 (s, 3H), 2.22 (s, 3H), 2.39 (s, 3H), 2.79 (t, 2H), 3.44 to 3.61 (m, 4H), 3.87 (s, 3H), 4.10 to 4.22 (m, 4H), 6.69 (d, 1H), 6.95 to 7.00 (m, 2H)

(6) Synthesis of N-chloroacetyl-N-{2-[4-(2-ethoxyethyl)-2-methylphenoxy]ethyl}-4-chloro-1,3-dimethyl-5-pyrazolecarboxamide (Compound 16)

In 10 ml of dried N,N-dimethylformamide was dissolved 1.5 g of N-{2-[4-(2-ethoxyethyl)-2-methylphenoxy]ethyl}-4-chloro-1,3-dimethyl-5-pyrazolecarboxamide. 0.3 g of sodium hydride (60% in oil) was added to the solution, and the mixture was stirred at 50° C. for 1 hour. The mixture was cooled to room temperature and 0.6 g of chloroacetyl chloride was added dropwise to the mixture. Then, the mixture was stirred at 50° C. for 2 hours.

After completion of the reaction, 10 ml of water was added slowly to the reaction mixture, and the mixture was extracted with ethyl acetate. The extract was washed with water and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene: ethyl acetate=9:1) to obtain 0.6 g of the title compound as pale yellow oily liquid.

$^1$H-NMR (CDCl$_3$, δppm) 1.20 (t, 3H), 2.05 (s, 3H), 2.24 (s, 3H), 2.78 (t, 2H), 3.49 (q, 2H), 3.75 (t, 3H), 3.86 (s, 3H), 4.12 (t, 2H), 4.22 (m, 2H), 4.52 (s, 2H), 6.69 (d, 1H), 6.95 (s, 1H), 6.96 (s, 1H)

(7) Synthesis of N-4-t-butylbenzoyl-N-{2-[4-(2-ethoxyethyl)-2-methylphenoxy]ethyl}-4-chloro-1,3-dimethyl-5-pyrazolecarboxamide (Compound 25)

In 10 ml of dried toluene was dissolved 1.2 g of N-{2-[4-(2-ethoxyethyl)-2-methylphenoxy]ethyl}-4-chloro-1,3-dimethyl-5-pyrazolecarboxamide. 0.25 g of sodium hydride (60% in oil) was added to the solution, and the mixture was refluxed under heating for 2 hours. The mixture was cooled to room temperature and 0.7 g of t-butylbenzoyl chloride was added dropwise to the mixture. Then, the mixture was refluxed under heating for 2 hours.

After completion of the reaction, 10 ml of water was added slowly to the reaction mixture under cooling, and the mixture was extracted with ethyl acetate. The extract was washed with water and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene: ethyl acetate=9:1) to obtain 1.1 g of the title compound as pale yellow oily liquid.

$^1$H-NMR (CDCl$_3$, δppm) 1.19 (t, 3H), 1.24 (s, 3H), 1.91 (s, 3H), 1.95 (s, 3H), 2.79 (t, 2H), 3.50 (q, 2H), 3.58 (t, 2H), 3.75 (s, 3H), 4.30 to 4.55 (m, 4H), 6.75 (d, 1H), 6.93 (s, 1H), 6.98 (d, 1H), 7.26 (t, 2H), 7.42 (d, 2H)

(8) Synthesis of N-acetyl-N-{2-[4-(2-ethoxyethyl)-2-methylphenoxy]ethyl}-1,3-dimethyl-5-pyrazolecarboxamide (Compound 33)

In 8 ml of acetic anhydride was dissolved 1.0 g of N-{2-[4-( 2-ethoxyethyl)-2-methylphenoxy]ethyl}-1,3- dimethyl-5-pyrazolecarboxamide. 0.05 ml g of conc. sulfuric acid was added to the solution, and the mixture was stirred at 100° C. for 4 hours.

After completion of the reaction, the reaction mixture was cooled to room temperature and made weakly acidic by adding a saturated sodium carbonate aqueous solution. The mixture was extracted with ethyl acetate, and the extract was washed with water and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene: ethyl acetate=9:1) to obtain 0.4 g of the title compound as pale yellow oily liquid.

$^1$H-NMR (CDCl$_3$, δppm) 1.20 (t, 3H), 2.04 (s, 3H), 2.28 (s, 3H), 2.79 (t, 3H), 3.50 (q, 2H), 3.58 (t, 2H), 3.99 (s, 3H), 4.12 (t, 2H), 4.27 (t, 2H), 6.32 (s, 1H), 6.68 (d, 1H), 6.96 (s, 1H), 6.98 (s, 1H)

(9) Synthesis of N-acetyl-N-{2-[4-(2-ethoxyethyl)-2-methylphenoxy]ethyl}-3-t-butyl-1-methyl-5-pyrazolecarboxamide (Compound 40)

In 8 ml of acetic anhydride was dissolved 1.1 g of N-{2-[4-(2-ethoxyethyl)-2-methylphenoxy]ethyl}-3-t-butyl-1-methyl-5-pyrazolecarboxamide, and the mixture was stirred at 100° C. for 4 hours.

After completion of the reaction, the reaction mixture was cooled to room temperature and made weakly acidic by adding a saturated sodium carbonate aqueous solution. The mixture was extracted with ethyl acetate, and the extract was washed with water and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene: ethyl acetate=9:1) to obtain 0.5 g of the title compound as pale yellow oily liquid.

$^1$H-NMR (CDCl$_3$, δppm) 1.20 (t, 3H), 1.25 (s, 3H), 2.00 (s, 3H), 2.22 (s, 3H), 2.78 (t, 2H), 3.45 to 3.59 (m, 4H), 4.00 (s, 3H), 4.12 (t, 2H), 4.28 (t, 2H), 6.35 (s, 1H), 6.68 (d, 1H), 6.95 (s, 1H), 6.96 (d, 1H)

(10) Synthesis of N-acetyl-N-{2-[4-(2-ethoxyethyl)-2-methylphenoxy]ethyl}-cyclopenta[1.2-c]-3-pyrazolecarboxamide (Compound 44)

In 5 ml of acetic anhydride was dissolved 1.1 g of N-{2-[4-(2-ethoxyethyl)-2-methylphenoxy]ethyl}-cyclopenta[1.2-c]-3-pyrazolecarboxamide. 0.05 ml g of conc. sulfuric acid was added to the solution, and the mixture was stirred at 110° C. for 10 hours.

After completion of the reaction, the reaction mixture was cooled to room temperature and made weakly acidic by adding a saturated sodium carbonate aqueous solution. The mixture was extracted with ethyl acetate, and the extract was washed with water and dried over anhydrous sodium sulfate. Then, the solvent was removed under reduced pressure.

The resulting crystals were recrystallized from toluene-n-hexane to obtain 0.5 g of the title compound as colorless powdery crystals.

$^1$H-NMR (CDCl$_3$, δppm) 1.19 (t, 3H), 1.98 (s, 3H), 2.21 (s, 3H), 2.34 (q, 2H), 2.52 (t, 2H), 2.70 (t, 2H), 2.78 (t, 2H), 3.49 (q, 2H), 3.56 (t, 2H), 4.03 (s, 3H), 4.11 (t, 2H), 4.22 (t, 2H), 6.66 (d, 1H), 6.94 (s, 1H), 6.96 (d, 1H)

(11) Synthesis of N-acetyl-N-{2-[4-(2-ethoxyethyl)-2-methylphenoxy]ethyl}-4-chloro-1-methyl-5-pyrazolecarboxamide (Compound 48)

In 8 ml of acetic anhydride was dissolved 1.0 g of N-{2-[4-(2-ethoxyethyl)-2-methylphenoxy]ethyl}-4-chloro-1-methyl-5-pyrazolecarboxamide, and the mixture was stirred at 100° C. for 4 hours.

After completion of the reaction, the reaction mixture was cooled to room temperature and made weakly acidic by adding a saturated sodium carbonate aqueous solution. The mixture was extracted with ethyl acetate, and the extract was washed with water and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene: ethyl acetate=9:1) to obtain 0.4 g of the title compound as pale yellow oily liquid.

$^1$H-NMR (CDCl$_3$, δppm) 1.20 (t, 3H), 2.08 (s, 3H), 2.40 (s, 3H), 2.80 (t, 2H), 3.50 (q, 2H), 3.92 (s, 3H), 4.11 to 4.25 (m, 6H), 6.70 (d, 1H), 6.95 (d, 1H), 6.97 (d, 1H), 7.41 (s, 1H)

(12) Synthesis of N-acetyl-N-{2-[4-(2-ethoxyethyl)-2,3-dimethylphenoxy]ethyl}-3-t-butyl-1-methyl-5-pyrazolecarboxamide (Compound 68)

In 20 ml of toluene was dissolved 3.0 g of N-{2-[4-(2-ethoxyethyl)-2,3-dimethylphenoxy]ethyl}acetamide. 0.6 g of sodium hydride (60% in oil) was added to the solution, and the mixture was refluxed under heating for 2 hours. The mixture was cooled to room temperature and 2.4 g of 3-t-butyl-1-methyl-5-pyrazolecarboxylic acid chloride was added dropwise to the mixture. Then, the mixture was stirred at 50° C. for 1 hour.

After completion of the reaction, 20 ml of water was added slowly to the reaction mixture under cooling, and the mixture was extracted with ethyl acetate. The extract was washed with water and dried over anhydrous sodium sulfate. Then, the solvent was removed under reduced pressure.

The resulting oily product was purified by silica gel column chromatography (Wako gel C-200 (trade name, manufactured by Wako Junyaku Co.), eluted by toluene: ethyl acetate=10:1). Then, the resulting crystals were recrystallized from n-hexane to obtain 2.1 g of the title compound as colorless powdery crystals.

$^1$H-NMR (CDCl$_3$, δppm) 1.21 (t, 3H), 1.26 (s, 3H), 1.95 (s, 3H), 2.18 (s, 3H), 2.22 (s, 3H), 2.86 (t, 2H), 3.46 to 3.54 (m, 4H), 4.00 (s, 3H), 4.11 (t, 2H), 4.29 (t, 2H), 6.32 (s, 1H), 6.49 (d, 1H), 6.94 (d, 1H)

(13) Syntheses of other compounds (I) in Table 2

According to the methods described in the above (1) to (12), the other compounds (I) in Table 2 shown below were synthesized.

The compounds thus synthesized are shown in Table 2.

TABLE 2

$$\text{(I)}$$

Structure: 1-methyl-pyrazole with R¹ at 3-position, R² at 4-position, 5-position connected to C(=O)-N(C(=O)R³)-CH₂CH₂-O-phenyl with R⁴, R⁵, R⁶ substituents.

| Compound | R¹ | R² | R³ | R⁴ | R⁵ | R⁶ | Physical property |
|---|---|---|---|---|---|---|---|
| 1 | CH₃ | Cl | CH₃ | CH₃ | CH₃ | H | $n_D^{19.1}$ 1.5426 |
| 2 | CH₃ | Cl | CH₃ | CH₃ | n-C₅H₁₁ | H | $n_D^{19.1}$ 1.5328 |
| 3 | CH₃ | Cl | CH₃ | CH₃ | —CH₂CH₂OCH₃ | H | $n_D^{25.5}$ 1.5419 |
| 4 | CH₃ | Br | CH₃ | CH₃ | —CH₂CH₂OCH₃ | H | $n_D^{21.4}$ 1.5534 |
| 5 | CH₃ | Cl | C₂H₅ | CH₃ | —CH₂CH₂OCH₃ | H | $n_D^{26.7}$ 1.5401 |
| 6 | CH₃ | Cl | C₆H₅ (phenyl) | CH₃ | —CH₂CH₂OCH₃ | H | $n_D^{20.0}$ 1.5715 |
| 7 | CH₃ | Cl | CH₃ | CH₃ | —CH₂CH₂OC₂H₅ | H | $n_D^{28.0}$ 1.5412 |
| 8 | CH₃ | Br | CH₃ | CH₃ | —CH₂CH₂OC₂H₅ | H | $n_D^{19.5}$ 1.5486 |
| 9 | CH₃ | Cl | C₂H₅ | CH₃ | —CH₂CH₂OC₂H₅ | H | $n_D^{24.1}$ 1.5355 |
| 10 | CH₃ | Cl | n-C₃H₇ | CH₃ | —CH₂CH₂OC₂H₅ | H | $n_D^{23.8}$ 1.5316 |
| 11 | CH₃ | Cl | n-C₄H₉ | CH₃ | —CH₂CH₂OC₂H₅ | H | $n_D^{19.9}$ 1.5253 |
| 12 | CH₃ | Cl | i-C₄H₉ | CH₃ | —CH₂CH₂OC₂H₅ | H | $n_D^{25.7}$ 1.5250 |
| 13 | CH₃ | Cl | t-C₄H₉ | CH₃ | —CH₂CH₂OC₂H₅ | H | $n_D^{23.2}$ 1.5286 |
| 14 | CH₃ | Cl | n-C₅H₁₁ | CH₃ | —CH₂CH₂OC₂H₅ | H | $n_D^{18.4}$ 1.5284 |
| 15 | CH₃ | Cl | n-C₈H₁₇ | CH₃ | —CH₂CH₂OC₂H₅ | H | $n_D^{24.0}$ 1.5102 |
| 16 | CH₃ | Cl | —CH₂Cl | CH₃ | —CH₂CH₂OC₂H₅ | H | $n_D^{21.8}$ 1.5461 |
| 17 | CH₃ | Cl | —CH₂OCH₃ | CH₃ | —CH₂CH₂OC₂H₅ | H | $n_D^{23.2}$ 1.5342 |
| 18 | CH₃ | Cl | cyclopropyl | CH₃ | —CH₂CH₂OC₂H₅ | H | $n_D^{24.1}$ 1.5411 |
| 19 | CH₃ | Cl | —CH=CHCH₃ | CH₃ | —CH₂CH₂OC₂H₅ | H | $n_D^{19.0}$ 1.5308 |
| 20 | CH₃ | Cl | C₆H₅ (phenyl) | CH₃ | —CH₂CH₂OC₂H₅ | H | $n_D^{24.1}$ 1.5622 |
| 21 | CH₃ | Cl | 2-Cl-C₆H₄ | CH₃ | —CH₂CH₂OC₂H₅ | H | $n_D^{21.1}$ 1.5590 |
| 22 | CH₃ | Cl | 3-Cl-C₆H₄ | CH₃ | —CH₂CH₂OC₂H₅ | H | $n_D^{21.2}$ 1.5579 |
| 23 | CH₃ | Cl | 4-Cl-C₆H₄ | CH₃ | —CH₂CH₂OC₂H₅ | H | $n_D^{20.3}$ 1.5673 |
| 24 | CH₃ | Cl | 4-CH₃-C₆H₄ | CH₃ | —CH₂CH₂OC₂H₅ | H |  |
| 25 | CH₃ | Cl | 4-(t-C₄H₉)-C₆H₄ | CH₃ | —CH₂CH₂OC₂H₅ | H | $n_D^{18.2}$ 1.5499 |

TABLE 2-continued

Structure (I):
Pyrazole with R¹ at 5-position, R² at 4-position, N-CH₃ at 1-position, connected via C(=O)-N(CH₂CH₂-O-phenyl(R⁴,R⁵,R⁶))-C(=O)-R³

| Compound | R¹ | R² | R³ | R⁴ | R⁵ | R⁶ | Physical property |
|---|---|---|---|---|---|---|---|
| 26 | CH₃ | Cl | 4-methoxyphenyl | CH₃ | —CH₂CH₂OC₂H₅ | H | |
| 27 | CH₃ | Cl | pyridyl | CH₃ | —CH₂CH₂OC₂H₅ | H | |
| 28 | CH₃ | Cl | 2-chloropyridyl | CH₃ | —CH₂CH₂OC₂H₅ | H | $n_D^{26.3}$ 1.5607 |
| 29 | CH₃ | Cl | —CH₂-phenyl | CH₃ | —CH₂CH₂OC₂H₅ | H | $n_D^{24.0}$ 1.5633 |
| 30 | CH₃ | Cl | CH₃ | CH₃ | —CH₂CH₂OC₃H₇-n | H | |
| 31 | CH₃ | Cl | CH₃ | CH₃ | —CH₂CH₂OCH₂CH=CH₂ | H | |
| 32 | CH₃ | Cl | CH₃ | CH₃ | —CH₂CH₂OCH₂C≡CH | H | $n_D^{26.7}$ 1.5489 |
| 33 | CH₃ | H | CH₃ | CH₃ | —CH₂CH₂OC₂H₅ | H | $n_D^{20.0}$ 1.5382 |
| 34 | CH₃ | H | C₂H₅ | CH₃ | —CH₂CH₂OC₂H₅ | H | m.p. 50 to 52° C. |
| 35 | C₂H₅ | Cl | CH₃ | CH₃ | —CH₂CH₂OC₂H₅ | H | m.p. 57 to 59° C. |
| 36 | C₂H₅ | H | CH₃ | CH₃ | —CH₂CH₂OC₂H₅ | H | $n_D^{26.7}$ 1.5325 |
| 37 | n-C₃H₇ | Cl | CH₃ | CH₃ | —CH₂CH₂OC₂H₅ | H | m.p. 66 to 68° C. |
| 38 | n-C₃H₇ | H | CH₃ | CH₃ | —CH₂CH₂OC₂H₅ | H | $n_D^{19.4}$ 1.5326 |
| 39 | i-C₃H₇ | H | CH₃ | CH₃ | —CH₂CH₂OC₂H₅ | H | $n_D^{26.6}$ 1.5291 |
| 40 | t-C₄H₉ | H | CH₃ | CH₃ | —CH₂CH₂OC₂H₅ | H | $n_D^{26.7}$ 1.5255 |
| 41 | cyclopropyl | Cl | CH₃ | CH₃ | —CH₂CH₂OC₂H₅ | H | m.p. 84 to 86° C. |
| 42 | CH₃ | Cl | CH₃ | CH₃ | —CH₂CH₂OC₂H₅ | 3-CH₃ | m.p. 68 to 70° C. |
| 43 | CH₃ | Cl | CH₃ | CH₃ | —CH₂CH₂OC₂H₅ | 6-CH₃ | $n_D^{16.5}$ 1.5333 |
| 44 | cyclopentyl | | CH₃ | CH₃ | —CH₂CH₂OC₂H₅ | H | m.p. 79 to 81° C. |
| 45 | cyclopentyl | | C₂H₅ | CH₃ | —CH₂CH₂OC₂H₅ | H | |
| 46 | 2-methylcyclopentyl | | CH₃ | CH₃ | —CH₂CH₂OC₂H₅ | H | m.p. 73 to 75° C. |
| 47 | 2-methylcyclopentyl | | C₂H₅ | CH₃ | —CH₂CH₂OC₂H₅ | H | |
| 48 | H | Cl | CH₃ | CH₃ | —CH₂CH₂OC₂H₅ | H | $n_D^{15.8}$ 1.5448 |
| 49 | CH₃ | H | n-C₃H₇ | CH₃ | —CH₂CH₂OC₂H₅ | H | |
| 40 | CH₃ | H | n-C₄H₉ | CH₃ | —CH₂CH₂OC₂H₅ | H | |
| 51 | CH₃ | H | n-C₅H₁₁ | CH₃ | —CH₂CH₂OC₂H₅ | H | $n_D^{19.4}$ 1.5251 |

TABLE 2-continued

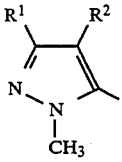

(I)

| Compound | R¹ | R² | R³ | R⁴ | R⁵ | R⁶ | Physical property |
|---|---|---|---|---|---|---|---|
| 52 | $CH_3$ | H | 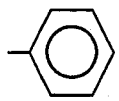 | $CH_3$ | $-CH_2CH_2OC_2H_5$ | H | m.p. 79 to 81° C. |
| 53 | $CH_3$ | H | 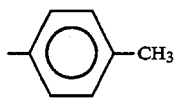 | $CH_3$ | $-CH_2CH_2OC_2H_5$ | H | m.p. 74 to 76° C. |
| 54 | $CH_3$ | H |  | $CH_3$ | $-CH_2CH_2OC_2H_5$ | H | m.p. 93 to 95° C. |
| 55 | $CH_3$ | H | $CH_3$ | H | H | H | m.p. 63 to 65° C. |
| 56 | $CH_3$ | H | $C_2H_5$ | H | H | H | $n_D^{22.2}$ 1.5335 |
| 57 | $CH_3$ | H | $CH_3$ | $CH_3$ | $n-C_4H_9$ | H | |
| 58 | $CH_3$ | H | $CH_3$ | $CH_3$ | $n-C_5H_{11}$ | H | |
| 59 | $CH_3$ | H | $CH_3$ | $CH_3$ | $-CH_2CH=CH_2$ | H | |
| 60 | $CH_3$ | H | $C_2H_5$ | Cl | $CH_3$ | 6-Cl | $n_D^{22.3}$ 1.5472 |
| 61 | $s-C_4H_9$ | H | $CH_3$ | $CH_3$ | $-CH_2CH_2OC_2H_5$ | H | $n_D^{25.4}$ 1.5248 |
| 62 | $s-C_4H_9$ | H | $C_2H_5$ | $CH_3$ | $-CH_2CH_2OC_2H_5$ | H | $n_D^{25.4}$ 1.4950 |
| 63 | $t-C_4H_9$ | H | $C_2H_5$ | $CH_3$ | $-CH_2CH_2OC_2H_5$ | H | $n_D^{25.4}$ 1.5029 |
| 64 | $t-C_4H_9$ | H | $CH_3$ | $CH_3$ | $n-C_5H_{11}$ | H | $n_D^{25.5}$ 1.5228 |
| 65 | $t-C_4H_9$ | H | $C_2H_5$ | $CH_3$ | $n-C_5H_{11}$ | H | $n_D^{25.5}$ 1.5103 |
| 66 | $t-C_4H_9$ | H | $CH_3$ | $CH_3$ | $-CH_2CH=CH_2$ | H | $n_D^{25.5}$ 1.5352 |
| 67 | $t-C_4H_9$ | H | $C_2H_5$ | $CH_3$ | $-CH_2CH=CH_2$ | H | $n_D^{25.5}$ 1.5269 |
| 68 | $t-C_4H_9$ | H | $CH_3$ | $CH_3$ | $-CH_2CH_2OC_2H_5$ | $3-CH_3$ | m.p. 78 to 80° C. |
| 69 | $t-C_4H_9$ | H | $C_2H_5$ | $CH_3$ | $-CH_2CH_2OC_2H_5$ | $3-CH_3$ | m.p. 59 to 60° C. |
| 70 | $t-C_4H_9$ | H | $CH_3$ | $CH_3$ | $CH_3$ | H | m.p. 66 to 68° C. |
| 71 | $t-C_4H_9$ | H | $C_2H_5$ | $CH_3$ | $CH_3$ | H | m.p. 75 to 77° C. |
| 72 | $CH_3$ | H | $i-C_3H_7$ | H | H | H | m.p. 89 to 91° C. |
| 73 | $t-C_4H_9$ | H | $i-C_3H_7$ | $CH_3$ | $-CH_2CH_2OC_2H_5$ | H | $n_D^{24.3}$ 1.5147 |
| 74 | $CH_3$ | H | 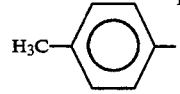 | $CH_3$ | $-CH_2CH_2OC_2H_5$ | H | $n_D^{24.5}$ 1.5379 |
| 75 | 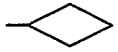 | H | $CH_3$ | $CH_3$ | $-CH_2CH_2OC_2H_5$ | H | m.p. 86 to 87° C. |
| 76 | $CH_3$ | H | 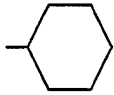 | $CH_3$ | $-CH_2CH_2OC_2H_5$ | H | $n_D^{21.5}$ 1.5368 |
| 77 | $CH_3$ | H | 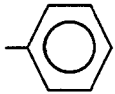 | $CH_3$ | $-CH_2CH_2OC_2H_5$ | H | $n_D^{21.6}$ 1.5344 |
| 78 | $t-C_4H_9$ | H |  | $CH_3$ | $-CH_2CH_2OC_2H_5$ | H | $n_D^{21.8}$ 1.5453 |
| 79 | $s-C_4H_9$ | Br | $CH_3$ | $CH_3$ | $-CH_2CH_2OC_2H_5$ | H | $n_D^{21.8}$ 1.5368 |

TABLE 2-continued (I)

structure: R¹, R² on pyrazole (N-N, CH₃), C(=O)-N(C(=O)-R³)-CH₂CH₂-O-phenyl(R⁴, R⁵, R⁶)

| Compound | R¹ | R² | R³ | R⁴ | R⁵ | R⁶ | Physical property |
|---|---|---|---|---|---|---|---|
| 80 | s-C₄H₉ | Br | C₂H₅ | CH₃ | —CH₂CH₂OC₂H₅ | H | $n_D^{21.9}$ 1.5298 |
| 81 | s-C₄H₉ | Br | n-C₃H₇ | CH₃ | —CH₂CH₂OC₂H₅ | H | $n_D^{22.0}$ 1.5057 |
| 82 | cyclopropyl | H | CH₃ | CH₃ | —CH₂CH₂OC₂H₅ | H | $n_D^{21.2}$ 1.5450 |
| 83 | phenyl | H | CH₃ | CH₃ | —CH₂CH₂OC₂H₅ | H | $n_D^{21.3}$ 1.5692 |
| 84 | phenyl | H | C₂H₅ | CH₃ | —CH₂CH₂OC₂H₅ | H | $n_D^{21.5}$ 1.5677 |
| 85 | cyclopropyl | H | C₂H₅ | CH₃ | —CH₂CH₂OC₂H₅ | H | m.p. 48 to 49° C. |
| 86 | phenyl | H | phenyl | CH₃ | CH₂CH₂OC₂H₅ | H | m.p. 95 to 97° C. |
| 87 | t-C₄H₉ | H | phenyl | CH₃ | n-C₅H₁₁ | H | $n_D^{21.8}$ 1.5495 |
| 88 | 4-Cl-phenyl | H | CH₃ | CH₃ | —CH₂CH₂OC₂H₅ | H | m.p. 80 to 82° C. |
| 89 | t-C₄H₉ | H | CH₃ | CH₃ | —CH₂CH₂OC₂H₅ | 6-CH₃ | $n_d^{24.8}$ 1.5190 |
| 90 | t-C₄H₉ | H | CH₃ | CH₃ | C₂H₅ | H | $n_D^{24.6}$ 1.5320 |
| 91 | t-C₄H₉ | H | CH₃ | CH₃ | n-C₃H₇ | H | $n_D^{24.7}$ 1.5276 |
| 92 | t-C₄H₉ | H | CH₃ | CH₃ | s-C₄H₉ | H | $n_D^{24.7}$ 1.5241 |
| 93 | t-C₄H₉ | H | cyclopropyl | CH₃ | —CH₂CH₂OC₂H₅ | H | $n_D^{25.4}$ 1.5302 |
| 94 | t-C₄H₉ | H | CH₃ | H | —CH₂—phenyl | H | $n_D^{25.4}$ 1.5591 |
| 95 | t-C₄H₉ | H | cyclobutyl | CH₃ | —CH₂CH₂OC₂H₅ | H | $n_D^{25.2}$ 1.5302 |
| 96 | CF₃ | H | CH₃ | CH₃ | —CH₂CH₂OC₂H₅ | H | m.p. 56 to 58° C. |
| 97 | t-C₄H₉ | H | 1,3,5-trimethylpyrazol-4-yl | CH₃ | —CH₂CH₂OC₂H₅ | H | $n_D^{23.1}$ 1.5341 |

TABLE 2-continued

General structure (I): pyrazole with $R^1$, $R^2$ substituents, N-CH$_3$, carboxamide linked to N(C(O)-R$^3$)-CH$_2$CH$_2$-O-phenyl(R$^4$, R$^5$, R$^6$)

| Compound | R¹ | R² | R³ | R⁴ | R⁵ | R⁶ | Physical property |
|---|---|---|---|---|---|---|---|
| 98 | t-C₄H₉ | Cl | CH₃ | CH₃ | —CH₂CH₂OC₂H₅ | H | $n_D^{24.8}$ 1.5277 |
| 99 | t-C₄H₉ | Cl | CH₃ | CH₃ | —CH₂CH₂OCOCH₃ | H | $n_D^{23.8}$ 1.5302 |
| 100 | t-C₄H₉ | H | CH₃ | CH₃ | —CH₂CH₂OCH₃ | H | $n_D^{23.8}$ 1.5295 |
| 101 | t-C₄H₉ | H | OCH₃ | CH₃ | —CH₂CH₂OC₂H₅ | H | $n_D^{23.2}$ 1.5194 |
| 102 | C₂H₅ | CH₃ | CH₃ | CH₃ | —CH₂CH₂OC₂H₅ | 3-CH₃ | $n_D^{23.4}$ 1.5367 |
| 103 | t-C₄H₉ | H | cyclopropyl | CH₃ | —CH₂CH₂OC₂H₅ | 3-CH₃ | $n_D^{26.7}$ 1.5308 |
| 104 | t-C₄H₉ | H | 3-C(CH₃)₃-1-methylpyrazol-5-yl | CH₃ | —CH₂CH₂OC₂H₅ | H | m.p. 118 to 120° C. |
| 105 | t-C₄H₉ | H | CH₃ | CH₃ | n-C₄H₉ | H | $n_D^{25.6}$ 1.5255 |
| 106 | t-C₄H₉ | H | CH₃ | H | t-C₄H₉ | H | $n_D^{24.0}$ 1.5279 |
| 107 | t-C₄H₉ | H | CH₃ | H | —O—C₆H₅ | H | $n_D^{24.0}$ 1.5610 |
| 108 | t-C₄H₉ | H | CH₃ | CH₃ | n-C₈H₁₇ | H | $n_D^{24.7}$ 1.5161 |
| 109 | t-C₄H₉ | H | CH₃ | CH₃ | —CH₂CH(C₂H₅)CH₂CH₃ | H | $n_D^{24.6}$ 1.5211 |
| 110 | t-C₄H₉ | H | —CH₂COOC₂H₅ | CH₃ | —CH₂CH₂OC₂H₅ | 3-CH₃ | $n_D^{25.5}$ 1.5165 |
| 111 | t-C₄H₉ | H | CH₃ | CH₃ | —CH₂CH₂OC₃H₇-n | H | $n_D^{23.4}$ 1.5234 |
| 112 | t-C₄H₉ | H | CH₃ | CH₃ | —CH₂CH₂OCH₂CH=CH₂ | H | $n_D^{23.4}$ 1.5295 |
| 113 | t-C₄H₉ | H | CH₃ | CH₃ | —CH₂CH₂OCH₂C≡CH₂ | H | $n_D^{23.5}$ 1.5343 |
| 114 | t-C₄H₉ | H | CH₃ | CH₃ | i-C₅H₁₁ | H | $n_D^{23.5}$ 1.5229 |
| 115 | t-C₄H₉ | H | CH₃ | Cl | Cl | 6-Cl | $n_D^{23.5}$ 1.5459 |
| 116 | t-C₄H₉ | H | H | CH₃ | —CH₂CH₂OC₂H₅ | 3-CH₃ | $n_D^{24.5}$ 1.5285 |
| 117 | t-C₄H₉ | H | CH₃ | CH₃ | —CH₂CN | 3-CH₃ | $n_D^{24.2}$ 1.5330 |
| 118 | t-C₄H₉ | H | CH₃ | H | —CH₂CH₂OC₂H₅ | H | $n_D^{24.9}$ 1.5262 |
| 119 | t-C₄H₉ | H | CH₃ | CH₃ | —CH₂OC₂H₅ | 3-CH₃ | $n_D^{24.3}$ 1.5285 |
| 120 | t-C₄H₉ | OCH₃ | CH₃ | CH₃ | —CH₂CH₂OC₂H₅ | H | $n_D^{25.0}$ 1.5236 |
| 121 | i-C₃H₇ | H | CH₃ | CH₃ | —CH₂CH₂OC₂H₅ | 3-CH₃ | m.p. 57 to 58.5° C. |
| 122 | t-C₄H₉ | CH₃ | CH₃ | CH₃ | —CH₂CH₂OC₂H₅ | H | $n_D^{23.0}$ 1.5260 |
| 123 | t-C₄H₉ | H | 4-Cl-3-CH₃-1-methylpyrazol-5-yl | CH₃ | —CH₂CH₂OC₂H₅ | H | $n_D^{24.2}$ 1.5414 |
| 124 | t-C₄H₉ | C₂H₅ | CH₃ | CH₃ | —CH₂CH₂OC₂H₅ | H | (Note 1) |
| 125 | t-C₄H₉ | NO₂ | CH₃ | CH₃ | —CH₂CH₂OC₂H₅ | H | $n_D^{23.2}$ 1.5362 |

(Note 1) ¹H-NMR (CDCl₃, δ ppm) 1.09(t, 3H), 1.20(t, 3H), 1.35(s, 9H), 2.11(s, 3H), 2.21(s, 3H), 2.58(q, 2H), 2.80(t, 3H), 3.49(t, 3H), 3.58(t, 3H), 3.75(s, 3H), 4.10 to 4.35(m, 4H), 6.70(d, 1H), 6.95(d, 1H), 6.97(s, 1H).

Among the compounds as mentioned in Table 2, the following compounds are preferred in the present invention.

N-acetyl-N-[2-(2,4-dimethylphenoxy)ethyl]-4-chloro-1,3-dimethyl-5-pyrazolecarboxamide (Compound 1), N-acetyl-N- {2- [4- ( 2-methoxyethyl ) -2-methylphenoxy ]ethyl }-4-bromo-1,3-dimethyl-5-pyrazolecarboxamide (Compound 4), N-propionyl-N- {2- [4 - ( 2-methoxyethyl ) -2 -methylphenoxy]-ethyl}-4-chloro-1, 3-dimethyl-5-pyrazolecarboxamide (Compound 5), N-benzoyl-N- {2- [4- (2-methoxyethyl) -2-methylphenoxy]ethyl}-4-chloro-1,3-dimethyl-5-pyrazolecarboxamide (Compound 6), N-acetyl-N- {2- [4 - ( 2-ethoxyethyl ) -2-methylphenoxy ]ethyl}-4-chloro-1,3-dimethyl-5-pyrazolecarboxamide (Compound 7), N-chloroacetyl-N- {2- [4 - ( 2-ethoxyethyl ) -2-methylphenoxy]-ethyl}-4-chloro-1,3-dimethyl-5-pyrazolecarboxamide (Compound 16), N-4 -t-butylbenzoyl-N- {2- [4 - ( 2-ethoxyethyl ) -2-methylphenoxy]ethyl}-4-chloro-1,3-dimethyl-5-pyrazolecarboxamide (Compound 25), N-acetyl-N- {2- [4- (2-ethoxyethyl) -2-methylphenoxy]ethyl}-1,3-dimethyl-5-pyrazolecarboxamide (Compound 33), N-acetyl-N- {2- [4- (2-ethoxyethyl) -2-methylphenoxy]ethyl}-3-t-butyl-1-methyl- 5-pyrazolecarboxamide (Compound 40), N-acetyl-N- {2- [4- (2-ethoxyethyl) -2-methylphenoxy]ethyl}-cyclopenta[1.2-c]-3-pyrazolecarboxamide (Compound 44), N-acetyl-N- {2- [4 - ( 2-ethoxyethyl ) -2-methylphenoxy]ethyl}-4-chloro-1-methyl-5-pyrazolecarboxamide (Compound 48), N-acetyl-N- {2- [4 - ( 2-ethoxyethyl ) -2,3-dimethylphenoxy]-ethyl}-3-t-butyl-1-methyl-5-pyrazolecarboxamide (Compound 68), N-propionyl-N-{2- [4- (2-ethoxyethyl)-2-methylphenoxy]ethyl}-4-chloro-1,3-dimethyl-5-pyrazolecarboxamide (Compound 9), N-cyclopropanecarbonyl-N- {2- [4- ( 2-ethoxyethyl ) -2-methylphenoxy]ethyl}- 4 -chloro- 1,3-dimethyl-5-pyrazolecarboxamide (Compound 18), N-acetyl-N- {2- [4 - ( 2-ethoxyethyl ) -2-methylphenoxy]ethyl}-3-isopropyl- 1-methyl-5-pyrazolecarboxamide (Compound 39), N-propionyl-N- {2- [4- (2-ethoxyethyl) -2-methylphenoxy]ethyl}-3-t-butyl-1-methyl-5-pyrazolecarboxamide (Compound 63), N-isobutyryl-N- {2- [4- (2-ethoxyethyl) -2-methylphenoxy]-ethyl}-3-t-butyl-1-methyl-5-pyrazolecarboxamide (Compound 73), N-cyclopropanecarbonyl-N- {2- [4- (2-ethoxyethyl)-2-methylphenoxy]ethyl}-3-t-butyl-1-methyl-5-pyrazolecarboxamide (Compound 93), N-acetyl-N-{2- [4- (2-n-propoxyethyl)-2-methylphenoxy]ethyl}-3-t-butyl-1-methyl-5-pyrazolecarboxamide (Compound 111), N-acetyl-N- {2- [4- (2-allyloxyethyl) -2-methylphenoxy]ethyl}-3-t-butyl-1-methyl-5-pyrazolecarboxamide (Compound 112), and N-acetyl-N-{2- [4- (2-propargyloxyethyl) -2-methylphenoxy]-ethyl}-3-t-butyl-1-methyl-5-pyrazolecarboxamide (Compound 113).

Particularly preferred are Compounds 40, 63, 68, 73 and 111.

Example 3 (Preparation of formulations)

(1) Preparation of granule

Five parts by weight of Compound 1 was uniformly mixed with 35 parts by weight of bentonite, 57 parts by weight of talc, 1 part by weight of Neopelex powder (trade name, produced by Kao K.K. ) and 2 parts by weight of sodium lignosulfonate, and then, the mixture was kneaded with addition of a small amount of water, followed by granulation and drying, to obtain a granule.

(2) Preparation of wettable powder

Ten parts by weight of Compound 1 was uniformly mixed with 70 parts by weight of kaolin, 18 parts by weight of white carbon, 1.5 parts by weight of Neopelex powder (trade name, produced by Kao K.K.) and 0.5 part by weight of Demol (trade name, produced by Kao K.K.), and then the mixture was pulverized to obtain a wettable powder.

(3) Preparation of emulsifiable concentrate

Twenty parts by weight of Compound 1 was uniformly mixed with 70 parts by weight of xylene by adding 10 parts by weight of Toxanone (trade name, produced by Sanyo Kasei Kogyo), and dissolved therein to obtain an emulsifiable concentrate.

(4) Preparation of dustable powder

Five parts by weight of Compound 1 was uniformly mixed with 50 parts by weight of talc and 45 parts by weight of kaolin to obtain a dustable powder.

Example 4 (Tests of effects)

(1) Test of effect on green rice leafhopper

The respective wettable powders of the compounds (I) shown in Table 2 prepared as in Example 3 were diluted to 300 ppm with water containing a surfactant (0.01%). In these respective chemicals, young seedlings of rice were dipped for 30 seconds, respectively, air-dried and put into the respective glass cylinders.

Subsequently, 10 green rice leafhoppers (4th instar nymphs) were placed in the respective cylinders. The cylinders were closed with porous caps and left to stand in a thermostat chamber at 25° C. After 4 days, insecticidal rate was determined by counting living and dead insects.

The insecticidal effect was evaluated by using 4 ranks depending on the range of insecticidal rate (A: 100% B: less than 100 to 80% C: less than 80 to 60% and D: less than 60%).

The results are shown in Table 3.

TABLE 3

| Test of effect on green rice leafhopper | |
|---|---|
| Compound | Effect |
| 3 | A |
| 4 | A |
| 5 | A |
| 7 | A |
| 8 | A |
| 9 | A |
| 10 | A |
| 17 | A |
| 20 | A |
| 29 | A |
| 32 | A |
| 35 | A |
| 43 | A |
| 46 | A |
| 112 | A |
| 113 | A |

(2) Test of effect on two-spotted spider mite female adult

The respective wettable powders of the compounds (I) shown in Table 2 prepared as in Example 3 were diluted to 300 ppm with water containing a surfactant (0.01%), and in these respective chemicals, kidney bean leaves (diameter: 20 mm) on which 10 two-spotted spider mite female adults were infested were dipped for 15 seconds, respectively.

Subsequently, these respective leaves were left to stand in a thermostat chamber at 25° C., and after 3 days, acaricidal rate was determined by counting living and dead mites in the respective leaves.

The acaricidal effect was evaluated by using 4 ranks depending on the range of acaricidal rate (A: 100% B: less than 100 to 80%, C: less than 80 to 60% and D: less than 60%).

The results are shown in Table 4.

TABLE 4

Test of effect on two-spotted spider mite female adult

| Compound | Effect |
|---|---|
| 1 | A |
| 2 | A |
| 3 | A |
| 4 | A |
| 5 | A |
| 6 | A |
| 7 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 22 | A |
| 23 | A |
| 25 | A |
| 28 | A |
| 29 | A |
| 32 | A |
| 33 | A |
| 34 | A |
| 35 | A |
| 36 | A |
| 39 | A |
| 40 | A |
| 43 | A |
| 51 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 73 | A |
| 74 | A |
| 76 | A |
| 77 | A |
| 78 | A |
| 79 | A |
| 82 | A |
| 86 | B |
| 89 | A |
| 90 | A |
| 91 | A |
| 92 | A |
| 93 | A |
| 94 | A |
| 95 | A |
| 96 | B |
| 98 | B |
| 100 | A |
| 101 | B |
| 103 | A |
| 104 | B |
| 105 | A |
| 106 | B |
| 107 | B |
| 108 | B |
| 110 | A |
| 111 | A |
| 112 | A |

TABLE 4-continued

Test of effect on two-spotted spider mite female adult

| Compound | Effect |
|---|---|
| 113 | A |
| 114 | A |
| 116 | A |
| 118 | A |
| 119 | A |
| 120 | A |
| 121 | A |
| 122 | A |
| 124 | A |

(3) Test of effect on two-spotted spider mite egg

Five female adults of two-spotted spider mites were infested on kidney bean leaf disk (diameter: 20 mm), then the adult mites were removed and the number of eggs produced was counted. On the other hand, the respective wettable powders of the compounds (I) shown in Table 2 prepared in the same manner as in Example 3 were diluted to 300 ppm with water containing a surfactant (0.01%), and in each chemical was dipped the leaf disk for 10 seconds, respectively.

Subsequently, these respective leaf disks were left to stand in a thermostat chamber at 25° C., and after 6 days, egg killing rate was determined by counting unhatched eggs in the respective leaves.

The egg killing effect was evaluated by using 4 ranks depending on the range of egg killing rate (A: 00%, B: less than 100 to 80%, C: less than 80 to 60% and D: less than 60%).

The results are shown in Table 5.

TABLE 5

Test of effect on two-spotted spider mite egg

| Compound | Effect |
|---|---|
| 1 | A |
| 2 | A |
| 3 | A |
| 5 | A |
| 7 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 22 | A |
| 23 | A |
| 25 | A |
| 28 | A |
| 29 | A |
| 32 | A |
| 33 | A |
| 34 | A |
| 35 | A |
| 36 | A |
| 37 | A |
| 39 | A |
| 40 | A |
| 43 | A |
| 44 | A |
| 48 | A |
| 51 | A |
| 61 | A |
| 62 | A |
| 63 | A |
| 64 | A |
| 66 | A |

TABLE 5-continued

Test of effect on two-spotted spider mite egg

| Compound | Effect |
| --- | --- |
| 67 | A |
| 68 | A |
| 69 | A |
| 70 | A |
| 73 | A |
| 74 | A |
| 76 | A |
| 77 | A |
| 78 | A |
| 79 | A |
| 80 | A |
| 81 | A |
| 82 | A |
| 83 | A |
| 85 | A |
| 89 | A |
| 90 | A |
| 91 | A |
| 92 | A |
| 93 | A |
| 94 | A |
| 95 | A |
| 96 | A |
| 98 | A |
| 100 | A |
| 101 | A |
| 102 | A |
| 103 | A |
| 105 | A |
| 106 | A |
| 108 | A |
| 110 | A |
| 111 | A |
| 112 | A |
| 113 | A |
| 114 | A |
| 116 | A |
| 118 | A |
| 119 | A |
| 120 | A |
| 121 | A |
| 122 | A |
| 124 | A |

(4) Test of controlling effect on blast (rice) (prevention effect)

In plastic flowerpots having a diameter of 6 cm, 10 rices (variety: Nihonbare) were grown per one flowerpot, and to the young plants at 1.5 leaf stage, the chemicals obtained by diluting the wettable powders of the compounds (I) shown in Table 2 prepared as in Example 3 to 500 ppm with water containing a surfactant (0.01%) were sprayed in an amount of 20 ml per one flowerpot, respectively.

After spraying, the rices were grown in a glass greenhouse for 2 days, and then a suspension of conidiospores of blast (rice) collected from infected leaves was sprayed uniformly to the plant leaves to be inoculated thereinto.

After inoculation, the rices were grown in a glass greenhouse at 28° C. for 5 days, and the degree of lesion of blast (rice) appeared on the leaves was examined.

The fungicidal effect was evaluated by using 6 ranks as compared with the degree of lesion in the non-treated district (0: all area is infected, 1: lesion area is about 60%, 2: lesion area is about 40%, 3: lesion area is about 20%, 4: lesion area is 10% or less and 5: no lesion is observed).

The results are shown in Table 6.

TABLE 6

Test of controlling effect on blast (rice) (prevention effect)

| Compound | Effect |
| --- | --- |
| 1 | 5 |
| 4 | 5 |
| 5 | 5 |
| 14 | 4 |
| 16 | 4 |
| 17 | 4 |
| 19 | 4 |
| 32 | 5 |
| 34 | 5 |
| 36 | 4 |
| 39 | 5 |
| 40 | 5 |
| 43 | 4 |
| 56 | 4 |
| 61 | 4 |
| 66 | 4 |
| 76 | 4 |
| 107 | 4 |
| 112 | 4 |
| 113 | 4 |
| 120 | 4 |
| Non-treated district | 0 |

(5) Test of controlling effect on powdery mildew (barley) (prevention effect)

In plastic flowerpots having a diameter of 6 cm, 10 barleys (variety: Kuromugi) were grown per one flowerpot, and to the young plants at 1.5 leaf stage, the chemicals obtained by diluting the wettable powders of the compounds (I) shown in Table 2 prepared as in Example 3 to 500 ppm with water containing a surfactant (0.01%) were sprayed in an amount of 20 ml per one flowerpot, respectively.

These barleys were grown in a glass greenhouse for 2 days, and then conidiospores of powdery mildew (barley) collected from infected leaves were dustable powdered uniformly over the respective plants to be inoculated thereinto.

Then, these plants were grown in a glass greenhouse for one week, and the degree of lesion of powdery mildew (barley) appeared on the respective first leaves was examined.

The evaluation results of the fungicidal effect are shown in Table 7 according to the 6 rank evaluation method described in the above (4).

TABLE 7

Test of controlling effect on powdery mildew (barley) (prevention effect)

| Compound | Effect |
| --- | --- |
| 4 | 4 |
| 5 | 4 |
| 8 | 4 |
| 13 | 5 |
| 14 | 4 |
| 16 | 5 |
| 17 | 5 |
| 19 | 4 |
| 28 | 5 |
| 36 | 4 |
| 43 | 4 |
| 44 | 5 |
| 76 | 4 |
| 82 | 5 |
| Non-treated district | 0 |

The novel phenoxyalkylamine derivative of the present invention has excellent insecticidal, acaricidal and fungicidal effects.

We claim:

1. A phenoxyalkylamine compound represented by the formula (I):

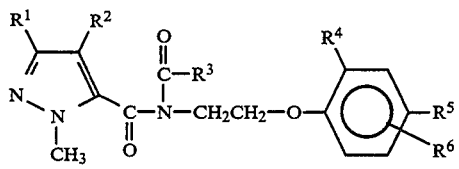

wherein $R^1$ represents an alkyl group having 1 to 8 carbon atoms; a cycloalkyl group having 3 to 8 carbon atoms; a hydrogen atom; a phenyl group which is unsubstituted or substituted by an alkyl group having 1 to 4 carbon atoms or a halogen atom; or a haloalkyl group having 1 to 4 carbon atoms; $R^2$ represents a halogen atom; a hydrogen atom; an alkyl group having 1 to 4 carbon atoms; an alkoxy group having 1 to 4 carbon atoms or a nitro group; $R^1$ and $R^2$ may be linked with each other and fused with carbon atoms of a pyrazole ring to which they are bonded to form a saturated 4- to 8-membered ring which is unsubstituted or substituted by an alkyl group having 1 to 4 carbon atoms; $R^3$ represents an alkyl group having 1 to 15 carbon atoms; a cycloalkyl group having 3 to 8 carbon atoms; a phenyl group which is unsubstituted or substituted by a halogen atom, an alkyl group having 1 to 8 carbon atoms or an alkoxy group having 1 to 4 carbon atoms; a haloalkyl group having 1 to 4 carbon atoms; an alkoxyalkyl group with 2 to 8 carbon atoms in total having an alkoxy group with 1 to 4 carbon atoms; an alkenyl group having 3 to 6 carbon atoms; a pyridyl group which is unsubstituted or substituted by a halogen atom; a benzyl group; an alkoxycarbonylalkyl group with 3 to 8 carbon atoms in total having an alkoxy group with 1 to 4 carbon atoms; a pyrazole group which is unsubstituted or substituted by an alkyl group having 1 to 8 carbon atoms or a halogen atom; or an alkoxy group having 1 to 4 carbon atoms; $R^4$ represents an alkyl group having 1 to 4 carbon atoms; a hydrogen atom or a halogen atom; $R^5$ represents an alkyl group having 1 to 20 carbon atoms; a hydrogen atom; an alkenyl group having 3 to 6 carbon atoms; a benzyl group; a phenoxy group; a halogen atom; a cyanomethyl group or —A—O—$R^7$ where A represents an alkylene group having 1 to 4 carbon atoms and $R^7$ represents an alkyl group having 1 to 6 carbon atoms; an alkenyl group having 3 to 6 carbon atoms, an alkynyl group having 3 to 6 carbon atoms or an acyl group having 2 to 5 carbon atoms; and $R^6$ represents a hydrogen atom; an alkyl group having 1 to 4 carbon atoms or a halogen atom.

2. The compound according to claim 1, wherein $R^1$ is an alkyl group having 1 to 6 carbon atoms, a cycloalkyl group having 3 to 6 carbon atoms, a phenyl group which is unsubstituted or substituted by a methyl group or a chlrorine atom; or a fluoroalkyl group having 1 to 4 carbon atoms; $R^2$ is a halogen atom; a hydrogen atom; an alkyl group having 1 to 4 carbon atoms; an alkoxy group having 1 to 4 carbon atoms or a nitro group; or $R^1$ and $R^2$ may be linked with each other and fused with carbon atoms of a pyrazole ring to which they are bonded to form a saturated 4- to 6-membered ring which is unsubstituted or substituted by an alkyl group having 1 to 4 carbon atoms.

3. The compound according to claim 1, wherein $R^1$ is an alkyl group having 1 to 4 carbon atoms, a cyclopropyl group, a phenyl group which is unsubstituted or substituted by a methyl group or a chlrorine atom; or a trifluoromethyl group; $R^2$ is a chlorine atom, a bromine atom; a hydrogen atom; a methyl group, an ethyl group; a methoxy group or a nitro group; or $R^1$ and $R^2$ may be linked with each other and fused with carbon atoms of a pyrazole ring to which they are bonded to form a saturated 5-membered ring which is unsubstituted or substituted by a methyl group.

4. The compound according to claim 1, wherein $R^3$ is an alkyl group having 1 to 10 carbon atoms; a cycloalkyl group having 3 to 6 carbon atoms; a phenyl group which is unsubstituted or substituted by a halogen atom, an alkyl group having 1 to 6 carbon atoms or an alkoxy group having 1 to 4 carbon atoms; a haloalkyl group having 1 to 4 carbon atoms; an alkoxyalkyl group with 2 to 6 carbon atoms in total having an alkoxy group with 1 to 3 carbon atoms; an alkenyl group having 3 or 4 carbon atoms; a pyridyl group which is unsubstituted or substituted by a chlorine atom; a benzyl group; an alkoxycarbonylalkyl group with 3 to 6 carbon atoms in total having an alkoxy group with 1 to 3 carbon atoms; a pyrazole group which is unsubstituted or substituted by an alkyl group having 1 to 6 carbon atoms or a chlorine atom; or an alkoxy group having 1 to 4 carbon atoms.

5. The compound according to claim 1, wherein $R^3$ is an alkyl group having 1 to 8 carbon atoms; a cycloalkyl group having 3 to 6 carbon atoms; a phenyl group which is unsubstituted or substituted by a fluorine atom, a chlorine atom, a bromine atom, an alkyl group having 1 to 4 carbon atoms or a methoxy group; a chloromethyl group; a methoxymethyl group; a 1-propenyl group; a 3-pyridyl group which is unsubstituted or substituted by a chlorine atom; a benzyl group; an ethoxycarbonylmethyl group; a 5-pyrazole group which is unsubstituted or substituted by an alkyl group having 1 to 4 carbon atoms or a chlorine atom; or a methoxy group.

6. The compound according to claim 1, wherein $R^4$ is an alkyl group having 1 to 4 carbon atoms; a hydrogen atom or a halogen atom; $R^5$ is an alkyl group having 1 to 15 carbon atoms; a hydrogen atom; an alkenyl group having 3 or 4 carbon atoms; a benzyl group; a phenoxy group; a halogen atom; a cyanomethyl group or —A—O—$R^7$ where A is an alkylene group having 1 to 4 carbon atoms and $R^7$ is an alkyl group having 1 to 4 carbon atoms, an alkenyl group having 3 or 4 carbon atoms, an alkynyl group having 3 or 4 carbon atoms or an acyl group having 2 to 4 carbon atoms and $R^6$ is a hydrogen atom; an alkyl group having 1 to 4 carbon atoms or a halogen atom.

7. The compound according to claim 1, wherein $R^4$ is a methyl group; a hydrogen atom or a chlorine atom; $R^5$ is an alkyl group having 1 to 10 carbon atoms; a hydrogen atom; an allyl group; a benzyl group; a phenoxy group; a chlorine atom; a cyanomethyl group or —A—O—$R^7$ where A is an ethylene group and $R^7$ is an alkyl group having 1 to 3 carbon atoms; an allyl group, a 2-propynyl group or an acyl group having 2 to 4 carbon atoms; and $R^6$ is a hydrogen atom; a methyl group or a chlorine atom.

8. The compound according to claim 1, wherein $R^5$ is —A—O—$R^7$ where A is an alkylene group having 1 to 3 carbon atoms and $R^7$ is an alkyl group having 1 to 3 carbon atoms, an alkenyl group having 3 or 4 carbon atoms, an alkynyl group having 3 or 4 carbon atoms or an acyl group having 2 to 4 carbon atoms.

9. The compound according to claim 1, wherein $R^5$ is a 2-methoxyethyl group, a 2-ethoxyethyl group, a 2-propoxyethyl group, a 2-allyloxyethyl group or a 2-propargyloxyethyl group.

10. The compound according to claim 1, wherein the compound is at least one selected from the group consisting of:

N-acetyl-N- [2- (2,4-dimethylphenoxy) ethyl ]-4-chloro-1,3-dimethyl-5-pyrazolecarboxamide, N-acetyl-N- {2- [4- (2-methoxyethyl) -2-methylphenoxy]ethyl}-4-bromo-1,3-dimethyl-5-pyrazolecarboxamide, N-propionyl-N-{2- [4- (2-methoxyethyl)-2-methylphenoxy]-ethyl}-4 -chloro- 1,3-dimethyl-5-pyrazolecarboxamide, N-benzoyl-N- {2- [4- (2-methoxyethyl) -2-methylphenoxy]ethyl}-4-chloro- 1,3 -dimethyl - 5 -pyrazolecarboxamide, N-acetyl-N- {2- [4- (2-ethoxyethyl) -2-methylphenoxy]ethyl}-4-chloro-1,3-dimethyl-5-pyrazolecarboxamide, N-chloroacetyl-N- {2- [4- (2-ethoxyethyl) -2-methylphenoxy]-ethyl}-4-chloro-1,3-dimethyl- 5-pyrazolecarboxamide, N-4-t-butylbenzoyl-N- {2- [4- (2-ethoxyethyl)-2-methylphenoxy]ethyl }-4- chloro-1,3-dimethyl-5-pyrazolecarboxamide, N-acetyl-N- {2- [4 - (2-ethoxyethyl) -2-methylphenoxy]ethyl}-1,3-dimethyl-5-pyrazolecarboxamide, N-acetyl-N- {2- [4- (2-ethoxyethyl) -2-methylphenoxy]ethyl}-3-t-butyl-1-methyl-5-pyrazolecarboxamide, N-acetyl-N- {2- [4- (2-ethoxyethyl)-2-methylphenoxy]ethyl}-cyclopenta[1.2-c]-3-pyrazolecarboxamide, N-acetyl-N- {2- [4- (2-ethoxyethyl)-2-methylphenoxy]ethyl}-4-chloro-1-methyl - 5 -pyrazole carboxamide, N-acetyl-N- {2- [4- (2-ethoxy ethyl)-2,3-dimethylphenoxy]-ethyl}-3-t-butyl- 1-methyl-5-pyrazolecarboxamide, N-propionyl-N- {2- [4-(2-ethoxyethyl)-2-methylphenoxy]ethyl}-4-chloro-1,3-dimethyl-5-pyrazolecarboxamide, N-cyclopropanecarbonyl-N-{2-[4-(2-ethoxyethyl)-2-methylphenoxy]ethyl}-4-chloro-1,3-dimethyl-5-pyrazolecarboxamide, N-acetyl-N-{2-[4-(2-ethoxyethyl)-2-methylphenoxy]ethyl}-3-isopropyl-1-methyl -5-pyrazolecarboxamide, N-propionyl-N-{2-[4-(2-ethoxyethyl)-2-methylphenoxy]-ethyl}-3-t-butyl-1-methyl-5-pyrazolecarboxamide, N-isobutyryl-N-{2- [4-(2-ethoxyethyl)-2-methylphenoxy]-ethyl}-3-t-butyl-1-methyl-5-pyrazolecarboxamide, N-cyclopropanecarbonyl-N-{2-[4-(2-ethoxyethyl)-2-methylphenoxy]ethyl}-3-t-butyl-1-methyl-5-pyrazolecarboxamide, N-acetyl-N-{2-[4-(2-n-propoxyethyl)-2-methylphenoxy]ethyl}-3-t-butyl-1-methyl-5-pyrazolecarboxamide, N-acetyl-N-{2-[4-(2-allyloxyethyl)-2-methylphenoxy]ethyl}-3-t-butyl-1-methyl-5-pyrazolecarboxamide, and N-acetyl-N-{2-[4-(2-propargyloxyethyl)-2-methylphenoxy]-ethyl}-3-t-butyl-1-methyl-5-pyrazolecarboxamide.

11. The compound according to claim 1, wherein the compound is at least one selected from the group consisting of:

N-acetyl-N-{2-[4-(2-ethoxyethyl)-2-methylphenoxy]ethyl}-3-t-butyl-1-methyl-5-pyrazolecarboxamide, N-propionyl-N-{2-[4-(2-ethoxyethyl)-2-methylphenoxy]ethyl}-4-chloro-1,3-dimethyl-5-pyrazolecarboxamide, N-acetyl-N-{2-[4-(2-ethoxyethyl)-2,3-dimethylphenoxy]-ethyl}-3-t-butyl-1-methyl-5-pyrazolecarboxamide, N-isobutyryl-N- {2- [4- (2-ethoxyethyl) -2-methylphenoxy]-ethyl}-3-t-butyl-1-methyl-5-pyrazolecarboxamide, and N-acetyl-N- {2- [4- ( 2-n-propoxyethyl)-2-methylphenoxy]ethyl}-3-t-butyl-1-methyl-5-pyrazolecarboxamide.

12. A chemical for controlling noxious organisms comprising the compound represented by the formula (I) according to claim 1 as an active ingredient and an insecticidally, acaricidally or fungicidally effective carrier.

* * * * *

UNITED STATES PATENT AND TRADEMARK OFFICE
CERTIFICATE OF CORRECTION

PATENT NO. : 5,380,744
DATED : January 10, 1995
INVENTOR(S) : Obata et al.

It is certified that error appears in the above-indentified patent and that said Letters Patent is hereby corrected as shown below:

Claim 10, column 41, line 40, change "pyrazole carboxamide" to --pyrazolecarboxamide--;

Column 41, line 41, change "ethoxy ethyl" to --ethoxyethyl--;

Column 42, lines 7 and 10, change "-ethyl" to --ethyl--.

Signed and Sealed this

Thirteenth Day of June, 1995

Attest:

BRUCE LEHMAN

*Attesting Officer*     *Commissioner of Patents and Trademarks*